United States Patent [19]
Toba et al.

[11] Patent Number: 5,500,453
[45] Date of Patent: Mar. 19, 1996

[54] (OXO)SULFONIUM COMPLEX, POLYMERIZABLE COMPOSITION CONTAINING THE COMPLEX, AND METHOD OF POLYMERIZING THE COMPOSITION

[75] Inventors: Yasumasa Toba; Madoka Yasuike; Takeo Yamaguchi, all of Tokyo, Japan

[73] Assignee: Toyo Ink Manufacturing Co., Ltd., Tokyo, Japan

[21] Appl. No.: 284,981

[22] Filed: Aug. 4, 1994

Related U.S. Application Data

[63] Continuation-in-part of Ser. No. 13,724, Feb. 3, 1993, abandoned.

[30]  Foreign Application Priority Data

Feb. 7, 1992 [JP] Japan .................................. 4-056831
Mar. 16, 1992 [JP] Japan .................................. 4-090185

[51] Int. Cl.⁶ .............................. C07F 5/02; C07F 9/02; C07F 2/50
[52] U.S. Cl. .......................... 522/25; 522/31; 522/121; 522/182; 522/186; 568/6; 430/2; 430/281.1
[58] Field of Search .................... 568/6; 522/31, 522/25, 121, 182, 186; 430/281, 2

[56]  References Cited

U.S. PATENT DOCUMENTS

| | | | |
|---|---|---|---|
| 3,028,361 | 4/1962 | Abrams | 260/454 |
| 3,567,453 | 3/1971 | Borden | 96/91 |
| 4,058,401 | 11/1977 | Crivello | 522/31 |
| 4,245,029 | 1/1981 | Crivello | 522/31 |
| 4,423,136 | 12/1983 | Crivello | 522/31 |
| 4,801,392 | 1/1989 | Adair | 522/31 |
| 4,863,757 | 9/1989 | Durand | 522/31 |
| 4,954,416 | 9/1990 | Wright | 522/31 |
| 5,047,568 | 9/1991 | Angelo | 568/6 |

OTHER PUBLICATIONS

Imahashi et al., Chemical Abstracts, vol. 114 (1991) p. 751, Abstract 218098g JP-A-02 157 760.
Crivello, J. Polymer Science: Polymer Letters Edition, vol. 17, 1979 pp. 759–764 "Triarylsulfonium Salts Photoinitators of Free Radical and Cationic Polymerization".
Ukhin "Formation of Trimethylsulfonium—" Chemical Abstracts, vol. 99, No. 13, Sep. 26, 1983 p. 543 Abstract 99:104722x.

*Primary Examiner*—Susan W. Berman
*Attorney, Agent, or Firm*—Wenderoth, Lind & Ponack

[57]  ABSTRACT

A sulfonium complex or oxosulfonium complex of the formula (1),

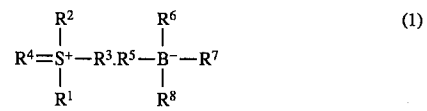

wherein $R^1$ is a benzyl group, a substituted benzyl group, a phenacyl group, a substituted phenacyl group, an aryloxy group, a substituted aryloxy group, an alkenyl group or a substituted alkenyl group, each of $R^2$ and $R^3$ is independently any one of groups defined as $R^1$, an alkyl group, a substituted alkyl group, an aryl group, a substituted aryl group, an aralkyl group, a substituted aralkyl group, an alkynyl group, a substituted alkynyl group, an alicyclic group, a substituted alicyclic group, an alkoxyl group, a substituted alkoxyl group, an alkylthio group, a substituted alkylthio group, an amino group or a substituted amino group, or $R^2$ and $R^3$ may bond together forming a ring structure, $R^4$ is an oxygen atom or lone pair, and each of $R^5$, $R^6$, $R^7$ and $R^8$ is independently an alkyl group, a substituted alkyl group, an aryl group, a substituted aryl group, an aralkyl group, a substituted aralkyl group, an alkenyl group or a substituted alkenyl group, provided that not all of $R^5$, $R^6$, $R^7$ and $R^8$ are aryl groups or substituted aryl groups.

8 Claims, 3 Drawing Sheets

(OXO)SULFONIUM COMPLEX, POLYMERIZABLE COMPOSITION CONTAINING THE COMPLEX, AND METHOD OF POLYMERIZING THE COMPOSITION

This application is a continuation-in-part of now abandoned application Ser. No. 08/013,724 filed Feb. 3, 1993, now abandoned.

FIELD OF THE INVENTION

The present invention relates to a novel sulfonium or oxosulfonium complex. More specifically, it relates to a novel sulfonium or oxosulfonium complex which is useful as a curing catalyst for photo-curable and heat-curable compounds, and particularly effective as a polymerization initiator for compounds having an ethylenically unsaturated bond.

Further, the present invention relates to a polymerizable composition containing the above sulfonium or oxosulfonium complex, and a method of polymerizing said composition. More specifically, it relates to a polymerizable composition which contains the above sulfonium or oxosulfonium complex and a radical-polymerizable, ethylenically unsaturated compound and can be optically or thermally cured for a short period of time to give cured products having excellent properties, for example, in the fields of an ink, a photosensitive form plate material, a photoresist, a direct printing material, a hologram material, a sealing agent and an adhesive, and a method of curing the above composition.

PRIOR ART

A variety of sulfonium complexes and oxosulfonium complexes have been hitherto reported, and these complexes are summarized in "Shin Jikken Kagaku Koza (New Experimental Chemistry Course)", Chemical Society of Japan, vol. 14, page 1,838 (1978, Maruzen Co., Ltd.), "Organic Sulfur Chemistry" (Synthesis Reaction), S. Ohae, page 237 (1982, Kagaku Dojin) and "Sulfur Ylides", B. M. Trost and L. S. Melvin, Jr., page 6 (1975, Academic Press). Further, Journal of American Chemical Society, vol. 106, page 4,121 (1984) discloses an arylalkylsulfonium complex. Journal of Chemical Society (C), page 682 (1970) discloses an aryloxysulfonium complex. European Patents 370693 and 331413 disclose arylalkylsulfonium complexes, JP-A-58-37003 discloses dialkylbenzylsulfonium hexafluoroantimonate, and JP-A-2-1470 discloses a P-hydroxyphenylalkylbenzylsulfonium complex. Further, Journal of Japanese Chemical Society, Vol. 87, No. 5, page 456 (1966) discloses a diarylsulfonium complex. Journal of Japanese Chemical Society, Vol. 87, No. 10, page 1,969, (1966) discloses a diphenylsulfonium complex. Journal of Chemical Society (C), page 682 (1970) discloses a diaryl(aryloxy)sulfonium complex. Further, European Patent 35969 discloses several (diaryl)oxosulfonium complex.

In each of the sulfonium complexes and oxosulfonium complexes disclosed in the above pieces of literature and patents, the anion portion is composed of inorganic anion derived from a halogen atom, $NO_3$, $BF_4$, $PF_6$, $SbF_6$, $SbCl_6$, $AsF_6$, $ClO_4$ and $HgI_3$, or anion derived from organic acids such as sulfonic acids and carboxylic acids, e.g., trifluoromethylsulfuric acid, p-toluenesulfonate and benzoate.

As sulfonium complex or oxosulfonium complex whose anion portion is composed of organic borate anion, U.S. Pat. No. 3,567,543 discloses dithioliumtetraphenyl borate, Journal of Chemical Society Chemical Communication, page 868 (1975) discloses triaminosulfoniumtetraphenyl borate and alkoxydiaminosulfoniumtetraphenyl borate, and Bulletin of Chemical Society of Japan, vol. 49, page 2,590 (1976) discloses ethoxymorpholinophenylsulfoniumtetraphenyl borate. In each of the above complexes, the anion portion is composed of tetraaryl borate.

On the other hand, concerning organic borate complexes, metal-borate complexes are disclosed in "Shin Jikken Kagaku Koza (New Experimental Chemistry Course)", Chemical Society of Japan, vol. 12, page 285 (1976, Maruzen Co., Ltd.), Justus Liebigs Annalen der Chemic. vol. 63, page 110 (1949), Journal of Organic Chemistry, vol. 29, page 1,971 (1964), Journal of Chemical Society, Perkin 2, page 1,225 (1978), JP-A-2-4804 and JP-A-2-3460. U.S. Pat. No. 4,343,891 discloses ammonium borate derivatives. JP-A-62-143044 and Journal of American Chemical Society, vol. 112, page 6,329 (1990) disclose dye-borate complex, and JP-A-3-704 discloses diaryliodonium-borate complex whose borate anion portion contains three aryl groups.

However, in sulfonium or oxosulfonium complex whose cation portion is composed of sulfonium or oxosulfonium, nothing other than tetraaryl borate is known as an anion portion.

A variety of sulfonium compounds and oxosulfonium compounds have been used as initiators for cationic polymerization, and these compounds are summarized, for example, in "Applications and Markets of UV.EB Curing Techniques", Radotech Society, page 79 (1989, CMC) and "Advances in Polymer Science", vol. 62, "Initiators-Poly-Reactrions-Optical Activity", J. V. Crivello (1984, Springer-Verlag).

Meanwhile, in recent years, it has been reported to use the above sulfonium compounds and oxosulfonium compounds as initiators for radical polymerization. For example, JP-B-63-2081 discloses triphenylsulfonium-hexafluorophosphate. JP-A-59-140203 discloses triarylsulfonium and diarylsulfonium compounds. JP-A-63-243102 discloses a variety of sulfonium compounds and oxosulfonium compounds.

It is considered that the sulfonium compounds and oxosulfonium compounds disclosed in the above pieces of literature or the above patents decompose in the carbon-sulfur bonding portion of their sulfonium cation under the action of heat or light, thereby to generate radicals. The anion portion of each of the above compounds is composed of inorganic anion such as $BF_4^-$, $PF_6^-$, $SbF_6^-$, $SbCl_6^-$ or $ClO_4^-$ or anion from sulfonic acid or carboxylic acid such as trifluoromethylsulfuric acid or p-toluenesulfonate.

However, concerning the use, as a polymerization initiator, of a sulfonium compound whose anion portion is composed of organic borate anion (borate), dithioliumtetraphenyl borate described in U.S. Pat. No. 3,567,453 and triphenylsulfonium triphenyl-n-butyl-borate described in JP-A-2-157760 are presumably all that are known.

On the other hand, concerning the use, as a radical polymerization initiator, of a complex having organic borate anion, there are known metal-borate complexes disclosed in JP-A-2-4804 and JP-A-2-3460, ammonium-borate complex disclosed in U.S. Pat. No. 4,343,891, a cationic dye-borate anion complex disclosed in JP-A-62-143044, and diaryliodonium-borate complexes disclosed in JP-A-2-157760, JP-A-2-166451 and JP-A-3-704. All of these complexes are considered to generate radicals by being decomposed in the carbon-boron bonding portion of their borate anion under the action of heat or light.

A polymerizable composition containing any one of the above polymerization initiators has the following problem when used in the fields of an ink, a photosensitive form plate material, a photoresist, a direct printing material, a hologram material, a sealing agent and an adhesive.

First, when the triaryl and diaryl sulfonium compounds disclosed in JP-B-63-2081 and JP-A-59-140203 and the sulfonium and oxosulfonium compounds disclosed in JP-A-63-243102 are used as initiators for radical polymerization, the anion portions of these compounds do not serve to generate radicals, and compositions containing these compounds are insufficient in sensitivity, since each anion portion is composed of inorganic anion such as $BF_4^-$, $PF_6^-$, $SbF_6^-$, $SbCl_6^-$ or $ClO_4^-$ or anion from sulfonic acid or carboxylic acid such as trifluoromethylsulfuric acid or p-toluenesulfonate.

The cationic dye-borate anion complex disclosed in JP-A-62-143044 has absorption in a visible light region, and it therefore decomposes under a general fluorescent lamp. It is therefore necessary to synthesize this complex in a dark place and use it also in a dark place. Since the region of wavelength at which the cationic dye-borate anion complex absorbs light is determined depending upon its cationic dye portion, it is necessary to select a cationic dye for forming a complex having photosensitivity in a desired absorption region. When the content of the cationic dye-borate anion complex in the polymerizable composition is increased to improve the light absorbing ability, the content of the borate portion which generates radicals consequently increases to decrease the polymerization degree of a polymer. Further, a composition containing this complex is insufficient in sensitivity.

The metal-borate complexes disclosed in JP-A-2-4804 and JP-A-2-3460 and the ammonium-borate complex disclosed in U.S. Pat. No. 4,343,891 hardly give compositions sufficient in sensitivity.

Further, the diaryliodonium-borate complexes disclosed JP-A-2-157760, JP-A-2-166451 and JP-A-3-704 are thermally unstable. The triphenyl or diarylsulfonium borate disclosed in JP-A-2-157760 does not effectively generate radicals due to its low reduction potential, and a composition containing it is insufficient in sensitivity.

It has been and is therefore desired to develop a polymerization initiator and a polymerizable composition which can overcome the above problems.

SUMMARY OF THE INVENTION

It is an object of the present invention to provide a novel sulfonium complex and a novel oxosulfonium complex.

It is another object of the present invention to provide a radical-polymerizable composition with high sensitivity so that the radical-polymerizable composition can be optically and/or thermally polymerized for a short period of time, and a method of polymerizing said composition.

It is further another object of the present invention to provide a polymerizable composition having excellent properties for use in an ink, a sealing agent, a photosensitive form plate material, a photoresist, a direct printing material, a hologram material, an adhesive, and the like, and a method of polymerizing said composition.

According to the present invention, there is provided a sulfonium complex or oxosulfonium complex of the formula (1),

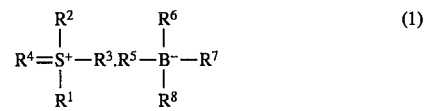

wherein $R^1$ is a benzyl group, a substituted benzyl group, a phenacyl group, a substituted phenacyl group, an aryloxy group, a substituted aryloxy group, an alkenyl group or a substituted alkenyl group, each of $R^2$ and $R^3$ is independently any one of groups defined as $R^1$, an alkyl group a substituted alkyl group, an aryl group, a substituted aryl group, an aralkyl group, a substituted aralkyl group, an alkynyl group, a substituted alkynyl group, an alicyclic group, a substituted alicyclic group, an alkoxyl group, a substituted alkoxyl group, an alkylthio group, a substituted alkylthio group, an amino group or a substituted amino group, or $R^2$ and $R^3$ may bond together forming a ring structure, $R^4$ is an oxygen atom or lone pair, and each of $R^5$, $R^6$, $R^7$ and $R^8$ is independently an alkyl group, a substituted alkyl group, an aryl group, a substituted aryl group, an aralkyl group, a substituted aralkyl group, an alkenyl group or a substituted alkenyl group, provided that not all of $R^5$, $R^6$, $R^7$ and $R^8$ are aryl groups or substituted aryl groups.

According to the present invention, there is also provided a polymerizable composition containing the above sulfonium complex or oxosulfonium complex and a radical-polymerizable, ethylenically unsaturated compound.

According to the present invention, there is further provided a method of polymerizing the above composition by heating or irradiation with light to generate active radicals.

DETAILED DESCRIPTION OF THE INVENTION

Figure 1:
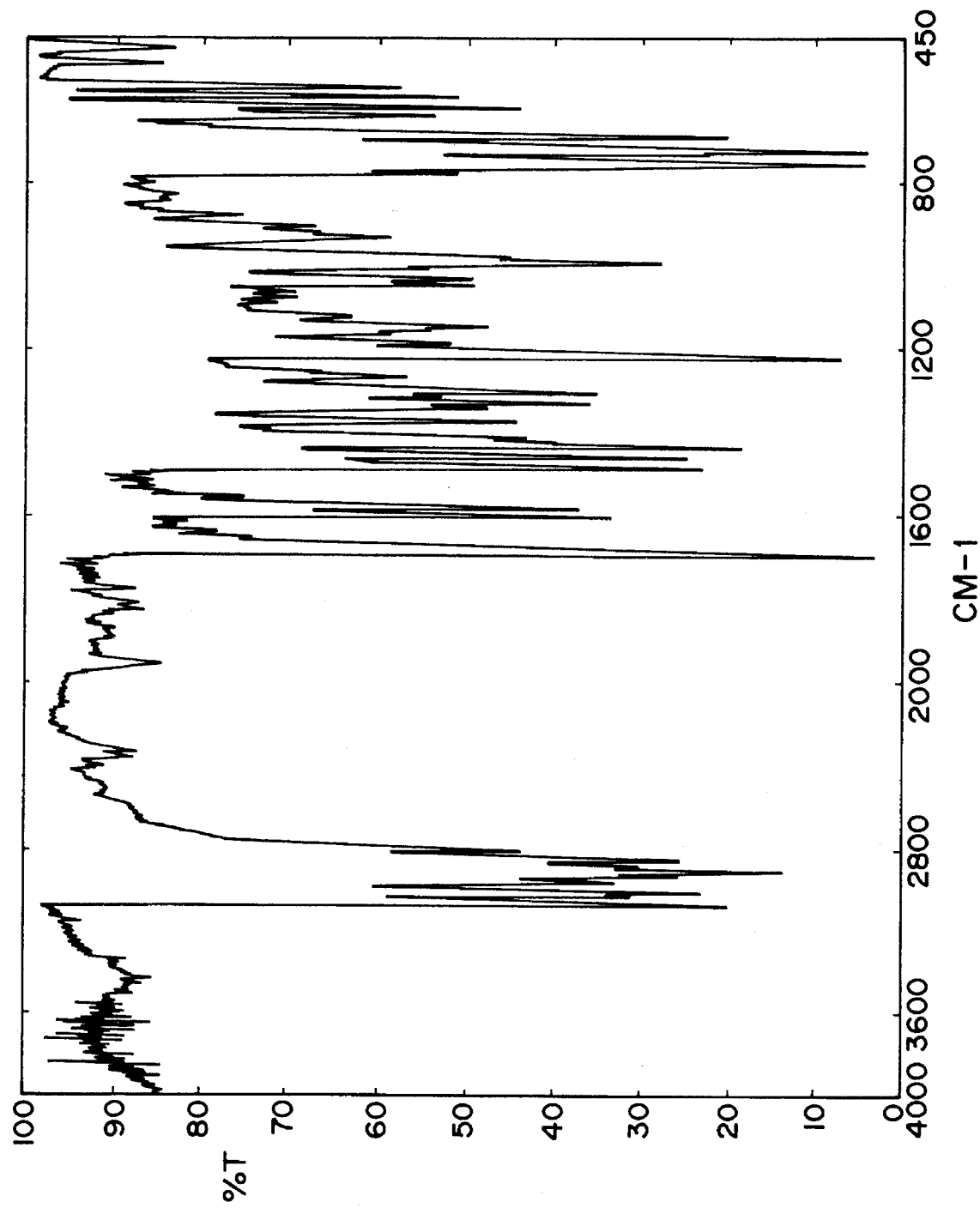
FIG. 1 shows the IR spectrum of a compound synthesized in Example 1 (in a KBr tablet).

The sulfonium complex or oxosulfonium complex (polymerization initiator) of the formula (1) is explained first. In the formula (1), $R^1$ is a benzyl group, a substituted benzyl group, a phenacyl group, a substituted phenacyl group, an aryloxy group, a substituted aryloxy group, an alkenyl group or a substituted alkenyl group, each of $R^2$ and $R^3$ is independently any one of groups defined as $R^1$, an alkyl group, a substituted alkyl group, an aryl group, a substituted aryl group, an aralkyl group, a substituted aralkyl group, an alkynyl group, a substituted alkynyl group, an alicyclic group, a substituted allcyclic group, an alkoxyl group, a substituted alkoxyl group, an alkylthio group, a substituted alkylthio group, an amino group or a substituted amino group, or $R^2$ and $R^3$ may bond together forming a ring structure, $R^4$ is an oxygen atom or lone pair, and each of $R^5$, $R^6$, $R^7$ and $R^8$ is independently an alkyl group, a substituted alkyl group, an aryl group, a substituted aryl group, an aralkyl group, a substituted aralkyl group, an alkenyl group or a substituted alkenyl group, provided that not all of $R^5$, $R^6$, $R^7$, and $R^8$ are aryl groups or substituted aryl groups.

The above optionally substituted alkyl group includes methyl, ethyl, propyl, isopropyl, butyl, isobutyl, sec-butyl, tert-butyl, pentyl, hexyl, octyl, decyl, dodecyl, octadecyl, allyl, acetonyl, phenacyl, salicyl, anisyl, cyanomethyl, chloromethyl, bromomethyl, trimethoxycarbonylmethyl, ethoxycarbonylmethyl, menthyl and pinanyl.

In the substituents, $R^1$, $R^2$ and $R^3$, on the sulfonium or oxosulfonium cation of the complex of the formula (1), the substituted benzyl group includes p-cyanobenzyl, p-hitrobenzyl, p-chlorobenzyl, p-hydroxybenzyl, p-methylbenzyl, p-methoxybenzyl, p-dimethylaminobenzyl and 1- or 2-naphthylmethylene, the substituted phenacyl group includes p-cyanophenacyl, p-nitrophenacyl, p-chlorophenacyl, p-hydroxyphenacyl, p-methylphenacyl and p-dimethylaminophenacyl, the aryloxy group and substituted aryloxy group include p-cyanophenoxy, p-nitrophenoxy, p-chlorophenoxy, phenoxy, p-tolyloxy, p-methoxyphenoxy and p-dimethylaminophenoxy, the alkenyl group and the substituted alkenyl group include vinyl, 1-propenyl, 1-butenyl and 3,3-dicyano-1-propenyl, the alkyl group and the substituted alkyl group include methyl, ethyl, propyl, isopropyl, butyl, isobutyl, sec-butyl, tert-butyl, pentyl, hexyl, octyl, decyl, dodecyl, octadecyl, allyl, salicyl, acetonyl, cyanomethyl, chloromethyl, bromomethyl, methoxycarbonylmethyl, ethoxycarbonylmethyl, menthyl and pinanyl, the aryl group and the substituted aryl group include phenyl, p-tolyl, xylyl, mesityl, cumenyl, p-methoxyphenyl, biphenylyl, naphthyl, anthryl, phenathoryl, p-cyanophenyl, p-nitrophenyl, 2,4-bis(trifluoromethyl)phenyl, p-fluorophenyl, p-chlorophenyl, p-dimethylaminophenyl and p-phenylthiophenyl, the alicyclic group and the substituted alicyclic group include cyclopentyl, cyclohexyl, norbornyl, bornyl and 1-, cyclohexenyl, the alkoxy group and the substituted alkoxy group include methoxy, ethoxy, n- or isopropoxy, n-, sec- or tert-butoxy, benzyloxy, p-cyanobenzyloxy, p-chlorobenzyloxy, p-nitrobenzyloxy, p-methylbenzyloxy and p-methoxybenzyloxy, the alkylthio group and the substituted alkylthio group include methylthio, ethylthio and butylthio, the substituted amino group includes methylamino, dimethylamino, diethylamino, cyclohexylamino, anilino, piperidino and morpholino, and the arylthio group and the substituted arylthio group include phenylthio, p-tolylthio and p-cyanophenylthio. Further, $R^2$ and $R^3$ may have a bonding cyclic structure, for example, a cyclic structure of alkylene such as tetramethylene, pentamethylene or 1,4-dichlorotetramethylene, ethylenedioxy, diethylenedioxy, adipoyl or ethylenedithio.

In the substituents, $R^5$, $R^6$, $R^7$, and $R^8$ on the organic boron anion of the complex of the formula (1), the alkyl group and the substituted alkyl group include methyl, ethyl, propyl, isopropyl, butyl, isobutyl, sec-butyl, tert-butyl, pentyl, hexyl, octyl, decyl, dodecyl, octadecyl, allyl and benzyl, the aryl and the substituted aryl group include phenyl, p-tolyl, xylyl, mesityl, cumenyl, p-methoxyphenyl, naphthyl, 2,4-bis(trifluoromethyl)phenyl, p-florophenyl, p-chlorophenyl and p-bromophenyl, the alkenyl group and the substituted alkenyl group include vinyl, 1-propenyl and 1-butenyl, and the alkynyl group and the substituted alkynyl group include ethenyl, 2-tert-butylethenyl and 2-phenylethenyl.

In the present invention, particularly preferred is a sulfonium complex or oxosulfonium complex of the formula (1) in which $R^1$ is benzyl group, substituted benzyl, phenacyl, substituted phenacyl, alkenyl or substituted alkenyl, each of $R^2$ and $R^3$ is independently alkyl, substituted alkyl, benzyl, substituted benzyl, phenacyl, substituted phenacyl, aryl or substituted aryl, $R^5$ is alkyl or substituted alkyl, and each of $R^6$, $R^7$ and $R^8$ is independently aryl or substituted aryl.

It is required to improve the sulfonium or oxosulfonium complex of the formula (1) in the optical and/or thermal decomposition efficiency, so that the above benzyl group, substituted benzyl group, phenacyl group, substituted phenacyl group, alkenyl group or substituted alkenyl group is introduced as $R^1$, and that the above alkyl group, substituted alkyl group, benzyl group, substituted benzyl group, phenacyl group, substituted phenacyl group, aryl group or substituted aryl group is introduced as each of $R^2$ and $R^3$. It is considered that these groups are preferentially and effectively decomposed from the sulfonium or oxosulfonium cation to generate radial, and the sensitivity is improved.

The improvement in the sensitivity can be estimated to some extent by measuring the polymerization initiator for a reduction potential by polarography or cyclic voltammetry, The higher the reduction potential is, the more easily, a polymerization initiator receives electrons. Therefore, the polymerization initiator is considered to decompose more effectively to generate radicals.

The reduction potentials of some sulfonium compounds are described in Journal of American Chemical Society, vol. 106, page 4,121 (1984), Journal of American Chemical Society, vol. 111, page 1,328 (1989), and "Advances in Polymer Science", vol . 62, "Initiators-Poly-Reactrions-Optical Activity", J. V. Crivello (1984, Springer-Verlag) and pieces of literature quoted therein.

For example, when measured by cyclic vol tammetry, methylphenylphenacylsulfonium cation has a reduction potential of −0.73 eV, and methylphenyl p-cyanobenzylsulfonium cation has a reduction potential of −0.95 eV, while triphenylsufonium cation has a lower reduction potential than the above cations, as low as −1.44 eV. As a result, a polymerizable composition containing a sulfonium cation with a relatively lower reduction potential such as a triphenylsulfonium cation cation also shows low sensitivity. Therefore, the combination of substituents ($R^1$, $R^2$ and $R^3$) on the sulfonium cation as in the case of triphenylsulfonium cation is not preferred.

However, when the borate anion of the complex of the formula (1) has a structure in which $R^5$ is an optionally substituted alkyl group and $R^6$, $R^7$ and $R^8$ are optionally substituted aryls, it is considered that $R^5$ on the borate anion, i.e., the optionally substituted alkyl group, undergoes preferential and effective cleavage from the borate anjou to improve the sensitivity.

On the other hand, when the borate anion of the complex of the formula (1) has a structure in which all of $R^5$, $R^6$, $R^7$ and $R^8$ are optionally substituted aryls, undesirably, the borate anion does not undergo effective clevage.

Therefore, the sulfonium complex and oxosulfonium complex of the formula (1) in the present invention, i.e., as polymerization initiators, preferably include combinations of the following cation portions and the following anion portions.

Examples of the cation portions, include dimethyl-tert-butylsulfonium, dimethylbenzylsulfonium, di-tertbutylbenzylsulfonium, didodecylbenzylsulfonium, dimethyl(p-chlorobenzyl)sulfonium, dibutyl (p-bromobenzyl)sulfonium, dimethyl (p-cyanobenzyl)sulfonium, dimethylphenacylsulfonium, di-tert-butylphenacylsulfonium, dimethyl (p-chlorophenacyl) sulfortinto, dimethyl (p-bromophenacyl)sulfonium, dimethyl (p-methoxyphenacyl)sulfonium, dimethyl(p-cyanophenacyl)sulfonium, dimethyl(2-phenyl-3,3-dicyanopropen-2-yl)sulfonium, dibutylethoxysulfonium, dimethylphenoxysulfonium, methyl(dimethylamino)(p-tolyl)sulfonium, dimethyl(methylthio)sulfonium, dimethylphenylthiosulfonium, methylphenylbenzylsulfonium, methylphenyl(p-cyanobenzyl)sulfonium, methylphenylphenacylsulfonium, methylphenyl(2-phenyl-3,3-dicyanopropen-2-yl)sulfonium, methylphenylethoxysulfonium, butylphenylphenoxysulfonium, dimethylamino-bis(p-tolyl)sulfonium, methylphenylmethyl thiosulfonium, diphenoxy(p-tolyl)sulfonium, bis(dimethylamino) (p-tolyl)sulfonium, tetramethylenephenacylsulfonium, tribenzylsulfonium, dimethylallylsulfonium, dibutylallylsulfonium, dimethyl(cyanomethyl)sulfonium, dimethylacetonylsulfonium, dimethylethoxycarbonylmethylsulfonium, dimethyl(2-ethoxycarbonyl)isopropylsulfonium, dimethyl(methylthiomethyl)sulfonium, diallylphenacylsulfonium, dimethylvinylsulfonium, tetramethylene-tert-butoxysulfonium, di-tert-butyl-N-cyclohexylaminosulfonium, diethyl-tert-butyloxosulfonium, dimethylbenzyloxosulfonium, dimethylphenacyloxosulfonium, dimethylphenoxyoxosulfonium, methylphenylbenzyloxosulfonium, methylphenylphenacyloxosulfonium, diphenoxy(p-tolyl)oxosulfonium, diphenylphenacylsulfonium, bis(p-tert-butylphenyl)phenacylsulfonium, bis(p-chlorophenyl)phenacylsulfonium, diphenyl(p-chlorophenacyl)sulfonium, diphenyl(p-nitrophcnacyl)sulfonium, diphenyl(m-methoxyphenacyl)sulfonium, diphenyl(p-cyanophenacyl)sulfonium, diphenyl[(1-naphthyl)carbonylmethyl] sulfonium, diphenylbenzylsulfonium, bis(p-tert-butylphenyl)benzylsulfonium, bis(p-chlorophenyl)benzylsulfonium, diphenyl(p-chlorobenzyl)sulfonium, diphenyl(p-nitrobenzyl)sulfonium, diphenyl(p-cyanobenzyl)sulfonium, diphenyl[(1-naphthyl)methyl] sulfonium, diphenylallylsulfonium, bis(p-tert-butylphenyl)allylsulfonium, bis(p-chlorophenyl)allylsulfonium, diphenyl(3,3-dicayno-2-phenyl-2-propenyl)sulfonium, diphenyl[3,3-bis(methoxycarbonyl)-2-phenyl-2-propenyl] sulfonium, diphenyl(3,3-dicyano-2-methyl-2-propenyl)sulfonium, diphenylphenacyloxosulfonium, bis(p-tert-butylphenyl)phenacyloxosulfonium, diphenyl(p-chlorophenyl)oxosulfonium, diphenyl(p-cyanophenacyl)oxosulfonium, diphenyl[(1-naphthyl)carbonylmethyl] oxosulfonium, diphenylbenzyloxosulfonium, bis(p-chlorophenyl)benzyloxosulfonium, diphenyl(p-cyanobenzyl)oxosulfonium, diphenylallyloxosulfonium, bis(p-tert-butylphenyl)allyloxosulfonium, diphenyl(3,3-dicyano-2-phenyl-2-propenyl)oxosulfonium and diphenyl[3,3-bis(methoxycarbonyl)-2-phenyl-2-propenyl]oxosulfonium.

Examples of the anion portions include tert-butyltriethylborate, phenyltriethylborate, tert-butyltributylborate, phenyltributylborate, tributylbenzylborate, diethyldibutylborate, methyltriphenylborate, ethyltriphenylborate, propyltriphenylborate, isopropyltriphenylborate, butyltriphenylborate, sec-butyltriphenylborate, tert-butyltriphenylborate, neopentyltriphenylborate, allyltriphenylborate, benzyltriphenylborate, vinyltriphenylborate, ethynyltriphenylborate, butyltrimesylborate, butyltri(p-methoxyphenyl)borate, butyltri(p-fluorophenyl)borate, butyltri(p-chlorophenyl)borate, butyltri(p-bromophenyl)borate, butyltris[3,5-bis(trifluoromethyl)phenyl]borate, sec-butyltri(p-methoxyphenyl)borate, sec-butyltri(p-fluorophenyl)borate, sec-butyltri(p-chlorophenyl)borate, sec-butyltri(p-chlorophenyl)borate, sec-butyltri(p-bromophenyl)borate, sec-butyltris[3,5-bis(trifluoropmethyl)phenylborate, tert-butyltri(p-methoxyphenyl)borate, tert-butyltri(p-fluorophenyl)borate, tert-butyltri(p-chlorophenyl)borate, tert-butyl tri(p-bromophenyl)borate, and tert-butyltris[3,5-bis(trifluoromethyl)phenyl] borate.

Accordingly, specific examples of the sulfonium complex or oxosulfonium complex of the formula (1) according to the present invention include dimethyl-tert-butylsulfonium-tert-butyltriethylborate, dimethylbenzylsulfonium-phenyltriethylborate, dimethyl(p-chlorobenzyl)sulfonium-methyltriphenylborate, dibutyl(p-bromobenzyl)sulfonium-isopropyltriphenylborate, dimethyl(p-cyanobenzyl)sulfonium-butyltriphenylborate, dimethylphenacylsulfonium-butyltriphenylborate, dimethylphenacylsulfonium-sec-butyltriphenylborate, di-tert-butylphenacylsulfonium-sec-butyltriphenylborate, dimethyl(p-chlorophenacyl)sulfonium-tertbutyltriphenylborate, dimethyl(p-bromophenacyl)sulfoniumbenzyltriphenylborate, dimethyl(2-phenyl-3,3-dicyanopropen-2-yl)sulfonium-butyltri(p-methoxyphenyl)borate, dibutylethoxysulfonium-butyltri(p-fluorophenyl)borate, dimethylphenoxysulfonium-butyltri(p-chlorophenyl)borate, methyl(dimethylamino)(p-tolyl)sulfonium-butyltri(p-bromophenyl)borate, dimethyl(methylthio)sulfoniumbutyltris[3,5-bis(trifluoromethyl)phenyl]borate, dimethylphenylthiosulfonium-sec-butyltri(p-methoxyphenyl)borate, methylphenyl(p-cyanobenzyl)sulfonium-sec-butyl tri(p-fluorophenyl)borate, methylphenylphenacylsulfonium-butyltriphenylborate, methylphenyl(2-phenyl-3,3-dicyanopropen-2-yl)sulfonium-tert-butyl tri(p-bromophenyl)borate, methylphenylethoxysulfonium-butyltriphenylborate, butylphenylphenoxysulfonium-butyltriphenylborate, dimethylaminobis(p-tolyl)sulfonium-sec-butyltri(p-bromophenyl)borate, tetramethylenephenacylsulfonium-sec-butyl triphenylborate, dimethylallylsulfoniumbutyl triphenylborate, dimethylcyanomethylsulfoniumbutyl triphenylborate, dimethylacetonylsulfoniumbutyl triphenylborate, dimethylethoxycarbonylmethylsulfonium-tert-butyltri(p-chlorophenyl)borate, dimethyl(methylthiomethyl)sulfonium-butyltriphenylborate, tetramethylene-p-cyanobenzylsulfonium-sec-butyltri-p-fluorophenylborate, dimethylbenzyloxosulfoniumbutyltriphenylborate, dimethylphenacyloxosulfonium-sec-butyltri(p-chlorophenyl)borate, methylphenylbenzyloxosulfonium-tert-butyltri(p-methoxyphenyl)borate, methylphenylphenacyloxosulfonium-tert-butyltri(p-fluorophenyl)borate, diphenylbenzylsulfonium-n-butyltriphenylborate, diphenyl(p-chlorobenzyl)sulfonium-n-butyl-tris(p-methoxyphenyl)borate, diphenyl(p-bromobenzyl)sulfonium-n-butyltris(p-fluorophenyl)borate, diphenyl(p-cyanobenzyl)sulfonium-n-butyltriphenylborate, bis(p-tert-butylphenyl)-benzylsulfonium-n-butyltris(p-bromophenyl)borate, bis(p-chlorophenyl)(p-cyanobenzyl)sulfonium-n-butyltriphenylborate, diphenyl(p-cyanobenzyl)sulfonium-phenyltri-n-butylborate, diphenyl(p-cyanobenzyl)-sulfonium-di-n-butyldiphenylborate, diphenyl(p-cyanobenzyl)sulfonium-vinyltriphenylborate, diphenyl(p-cyanobenzyl)sulfonium-sec-butyltriphenylborate, diphenyl(p-cyanobenzyl)sulfonium-cyclohexyltriphenylborate, diphenylphenacylsulfonium-n-butyltriphenylborate, diphenyl(p-chlorophenacyl)sulfonium-n-butyltriphenylborate, diphenyl(p-bromophenacyl)sulfonium-n-butyltriphenylborate, diphenyl(p-methoxyphenacyl)sulfonium-n-butyltriphenylborate, diphenyl(p-cyanophenacyl)sulfonium-cyclohexyl-tris-(p-methoxyphenyl)borate, bis(p-tert-butylphenyl)phenacylsulfonium-sec-butyl-tris(p-fluorophenyl)borate, bis(p-methoxyphenyl)(p-chlorophenacyl)sulfonium-di-n-butyldiphenylborate, bis(p-chlorophenyl)(p-bromophenacyl)sulfoniumbenzyltriphenylborate, bis(p-methylphenyl)(p-methoxyphenacyl)sulfonium-tert-butyltriphenylborate, bis(p-tert-butylphenacyl)(p- cyanophenacyl)sulfonium-benzyltri-n-butylborate, diphenylallylsulfonium-n-butyltriphenylborate, diphenyl(2-methyl-3,3-dicyano-2-propenyl)sulfonium-2-phenylethynyltriphenylborate, diphenyl(2-phenyl-3,3-dicyano-2-propenyl)sulfonium-n-butyltriphenylborate, diphenyl[2-phenyl-3,3-bis(methoxycarbonyl)-2-propenyl]sulfonium-secbutyltriphenylborate, bis(p-chlorophenyl)allylsulfoniumtriethylborate, bis(p-tert-butylphenyl)(2-methyl-3,3-dicyano-2-propenyl)sulfonium-di(sec-butyl)diphenylborate, bis(p-methylphenyl)(2-phenyl-3,3-dicyano-2-propenyl)sulfonium-n-butyltriphenylborate, diphenylacetonylsulfonium-n-butyltriphenylborate, diphenylcyanomethylsulfonium-n-butyltriphenylborate, diphenylmethoxycarbonylmethylsulfonium-n-butyltriphenylborate, diphenylsulfomethylsulfonium-methyl-tris(p-fluorophenyl)borate, diphenyl-p-toluenesulfonylmethylsulfonium-dicyclohexyldiphenylborate, diphenyl(trimethylammoniumylmethyl)sulfonium-bis(n-butyltriphenylborate), diphenyl(n-triphenylphenacylphosphoniumylmethyl)sulfonium-bis(n-butyl triphenylborate), diphenyl(phenyliodoniumylethynyl)sulfonium-bis(butyltriphenylborate), diphenylbenzyloxosulfonium-n-butyltriphenylborate, diphenyl(p-cyanobenzyl)oxosulfonium-n-butyltriphenylborate, diphenyl(p-cyanobenzyl)oxosulfonium-sec-butyl triphenylborate, diphenyl(p-cyanobenzyl)oxosulfoniumcyclohexyl-tris(p-fluorophenyl)borate, diphenylphenacyloxosulfonium-n-butyltriphenylborate, diphenyl(p-chlorophenacyl)phenylborate-sec-butyltris(p-fluorophenyl)borate, bis(p-tertbutylphenyl)phenacyloxosulfonium-octyl-tris(p-fluorophenyl)borate, diphenylallyloxosulfonium-n-butyl triphenylborate, diphenyl(2-phenyl-3,3-dicyano-2-propenyl)oxosulfonium-tert-butyltriphenylborate, diphenylmethoxycarbonylmethyloxosulfonium-n-butyl triphenylborate, diphenyl(trimethylammoniumylmethyl)-oxosulfonium-bis(n-butyltriphenylborate) and diphenyl(triphenylphenacyl-oxophosphoniumylmethyl)-oxosulfonium-bis(n-butyltriphenylborate). However, the sulfonium or oxosulfonium complex of the formula (1) shall not be limited to the above complexes.

Most of the sulfonium or oxosulfonium complexes of the formula (1) are hardly active to light in the region of from near ultraviolet light to near infrared light, since they generally show no absorption to light having a wavelength longer than that of ultraviolet light. However, the use of a substitutional group of a fused aromatic group such as naphthyl, anthranyl, phenathryl or anthryl, or other proper substituent as any one of $R^1$ to $R^8$ except for $R^4$ can enhance the spectral sensitivity to light having from visible to near infrared wavelength.

Further, the present invention provides a polymerizable composition containing the sulfonium or oxosulfonium complex of the formula (1) and a radical-polymerizable, ethylenically unsaturated compound. The sensitivity of the polymerizable composition to light in the region of from ultraviolet light to near infrared light can be highly improved by incorporating the above sulfonium or oxosulfonium complex in combination with a sensitizer having absorption to light in the region of from ultraviolet light to near infrared light.

Specific examples of the above sensitizer include unsaturated ketones typified by chalcone and its derivatives and dibenzalacctone, 1,2-diketone typified by benzyl and camphorquinone, benzoins, fluorenes, naphthoquinones, anthraquinones, xanthenes, thioxanthenes, xanthones, thioxanthones, coumarins, ketocoumarins, polymethine dyestuffs such as cyanins and merocyanines, oxonols, styryls, acridines, azines, thiazines, oxazines, indolines, azulencs, azelcniums, squaliliums, porphyrins including tetraphenylporphyrin and tetrabenzoporphyrin, triarylmethanes, tetrapyradinoporphyrazine, phthalocyanines, tetraazaporphyrazines, tetraquinoxalinoprophyrazine, napthalocyanine, subphthalocyaninc, pyryliums including thiopyrylium, tetraphyllines, annuleries, spiropyrans, spirooxazines, thiospiropyrans, metal arene complexes, triazine compounds with trihalogcnomethyl groups and chromophore, and organic ruthenium complexes. Further, examples of the above sensitizer include those dyestuffs and sensitizers described in "Shikiso (Dyestuff) Handbook", S. Okawara, et al (1986, Kodansha Ltd., Publishers), "Kinosei Shikiso no Kagaku (Chemistry on Functional Dyestuffs", S. Okawara, et al (1981, CMC), and "Tokushu Kino Zairyo (Special Functional Materials), C. Ikemori et al (1986, CMC). Furthermore, there are included other dyestuffs and sensitizers having absorption in the region of from ultraviolet light to near infrared light. The above dyestuffs and sensitizers may be used alone or in combination.

The above radical-polymerizable, ethylenically unsaturated compound used in the present invention may be any compound that has at least one radical-polymerizable, ethylenically unsaturated bond in the molecule. It may be any one of a monomer, oligomer and polymer. These compounds may be used alone or in combination.

The above radical-polymerizable, ethylenically unsaturated compound is selected from unsaturated carboxylic acids such as acrylic acid, methacrylic acid, iraconic acid, crotonic acid, isocrotonic acid and maleic acid, salts, esters, urethanes, amides and anhydrides of these unsaturated carboxylic acids, acrylonitrile, styrene, unsaturated polyesters, unsaturated polyethers, unsaturated polyamides, and unsaturated polyurethanes.

Specific examples of the radical-polymerizable, ethylenically unsaturated compound include acrylic acid derivatives such as 2-ethylhexyl acrylate, 2-hydroxyethyl acrylate, butoxyethyl acrylate, carbitol acrylate, cyclohexyl acrylate, tetrahydrofurfuryl acrylate, benzyl acrylate, bis(4-acryloxypolyethoxyphenyl)propane, neopentyl glycol diacrylate, 1,6-hexanediol diacrylate, ethylene glycol diacrylate, diethylene glycol diacrylate, triethylene glycol diacrylate, tetraethylene glycol diacrylate, polyethylene glycol diacrylate, polypropylene glycol diacrylate, pentaerythritol diacrylate, pentaerythritol triacrylate, pentaerythritol tectraacrylate, dipentaerythritol tetraacrylate, trimethylolpropane triacrylate, tetramethylolmethane tetraacrylate, oligoester acrylate, N-methylol acrylamide, diacetone acrylamide and epoxy acrylate, methacrylic acid derivatives such as methyl methacrylate, n-butyl methacrylate, 2-ethylhexyl methacrylate, lauryl methacrylate, allyl methacrylate, glycidyl methacrylate, benzyl methacrylate, dimethylaminomethyl methacrylate, 1,6-hexanediol dimethacrylate, ethylene glycol dimethacrylate, triethylene glycol dimethacrylate, polyethylene glycol dimethacrylate, polypropylene glycol dimethacrylate, trimethylolethane trimethacrylate, trimethylolpropane trimethacrylate and 2,2-bis(4-methacryloxypolyethoxyphenyl)propane, and derivatives of allyl compounds such as allyl glycidyl ether, diallyl phthalate and triallyl trimellitate. Further, examples of the above radical-polymerizable, ethylenically unsaturated compound include those commercially available or industrially known, radical-polymerizable and crosslinkable monomers, oligomers and polymers described in "Handbook on Crosslinking Agents", S. Yamashita, et al (1981, Taiseisha), "UV.EB Curing Handbook (Materials)", K. Karo (1985, Kobunshi Kankokai), "Applications and Markets of UV.EB Curing Techniques", Radotech Society, page 79 (1989, CMC), page 79 (1989, CMC), "Shin-KankoseiJushi no Jissai Gijutsu (New Actual techniques on Photosensitive Resins)", K. Akamatsu (1987, CMC), "Netsukokasei Kobunshi no Seimitsuka", T. Endo (1986, CMC), and "Polyester Resin Handbook", E. Takiyama (1988, Nikkan Kogyo Shinbunsha).

In the polymerizable composition of the present invention, the amount of the sulfonium or oxosulfonium complex of the formula (1) is preferably 0.01 to 30 parts by weight, more preferably 0.1 to 10 parts by weight, per 100 parts by weight of the radical-polymcrizable, ethylenically unsaturated compound.

The polymerizable composition of the present invention can be used in a manner in which it is mixed with a binder such as an organic polymer and the resultant mixture is applied onto to a glass plate, an aluminum plate, other metal plate or a polymer film such as a polyethylene terephthalate film.

The above binder includes polymers and copolymers such as polyacrylates, poly-a-alkyl acrylates, polyamides, polyvinyl acetals, polyformaldehydes, polyurethanes, polycarbonates, polystyrenes and polyvinyl esters. Specific examples of the above binder include polymethacrylate, polymethyl methacrylate, polyethyl methacrylate, polyvinyl carbazole, polyvinyl pyrrolidone, polyvinyl butylal, polyvinyl acetate, a novolak resin, a phenolic resin, an epoxy resin, an alkyd resin and other industrially known organic polymers described in "Shin-KankoseiJushi no Jissai Gijutsu (New Actual techniques on Photosensitive Resins)", K. Akamatsu (1987, CMC) and "10,188 Chemical Products", pages 657–767 (Kagaku Kogyo Nipposha, 1988).

The polymerizable composition of the present invention can be used in combination with other polymerization initiator for improving its sensitivity.

Examples of the above "other polymerization initiator" include triazine derivatives described in JP-B-59-1281, JP-B-61-9621 and JP-A 60-60104, organic peroxides described in JP-A-59-1504 and JP-A-61-243807, diazonium compounds described in Japanese Patent Publications Nos. 43-23684, 44-6413 and 47-1604 and U.S. Pat. No. 3,567,453, organic azide compounds described in U.S. Pat. Nos. 2,848,328, 2,852,379 and 2,940,853, orthoquinonediazides described in Japanese Patent Publications Nos. 36-22062, 37-13109, 38-18015 and 45-9610, onium compounds including iodonium compounds, described in JP-B-55-39162, JP-A-59-140203 and "Macromolecules", vol. 10, page 1,307 (1977), azo compounds described in JP-A-59-142205, metal arene complexes described in JP-A-1-54440, European Patent 109851, European Patent 126712 and "Journal of Imaging Science", vol. 30, page 174 (1986), titanocenes described in JP-A-61-151197, transition metal complexes containing transition metal such as ruthenium, described in "Coordination Chemistry Review", vol. 84, pages 85–277 (1988) and JP-A-2-182701, aluminate complexes described in JP-A-3-209477, borate compounds described in JP-A-2-157760, 2,4,5-triarylimidazole dimer described in JP-A-55-127550 and JP-A-60-202437, carbon tetrabromide, and organic halogenated compounds described in JP-A-59-107344. The amount of the above "other polymerization initiator" is preferably 0.01 to 10 parts by weight per 100 parts by weight of the radical-polymerizable, ethylenically unsaturated compound.

The polymerizable composition of the present invention may contain a heat-polymerization inhibitor for preventing the polymerization during its storage.

Specific examples of the above heat-polymerization inhibitor include p-methoxyphenol, hydroquinone, alkyl-substituted hydroquinone, catechol, tert-butyl catechol and phenothiazine. The amount of the heat-polymerization inhibitor is preferably 0.001 to 5 parts by weight per 100 parts by weight of the radical-polymerizable, ethylenically unsaturated compound, The polymerizable composition of the present invention may further contain a polymerization promoter and chain transfer catalyst typified by amine, thiol and disulfide.

Specific examples of the above polymerization promoter and chain transfer catalyst include amines such as N-phenylglycine, triethanolamine and N,N-diethylaniline, thiols described in U.S. Pat. No. 4,414,312 and JP-A-64-13144, disulfides described in JP-A-2-291561, thiones described in U.S. Pat. No. 3,558,322 and JP-A-64-17048, and o-acyl thiohydroxamates and N-alkoxyoyridinethiones described in JP-A-2-291560.

Further, the polymerizable composition of the present invention may be used as a mixture prepared by incorporating thereto any one of oxygen scavenger and reducing agents such as a dye, an organic pigment, an inorganic pigment, phosphine, phosphonate and phosphite, an anti-blushing agent, a discoloration inhibitor, a halation inhibitor, a fluorescent brightener, a surfactant, a colorant, a filler, a plasticizer, an antioxidant, a UV absorbent, a foaming agent, a mold preventer, an antistatic agent, a magnetic material, additives having other properties, and a diluent.

The polymerizable composition of the present invention is polymerized by applying optical energy such as ultraviolet light, visible light and near infrared light and/or heat energy by heating or from a thermal head in a solvent inert to the polymerization initiator and the radical-polymerizable, ethylenically unsaturated compound, whereby an intended polymer product can be obtained. In addition, the terms, ultraviolet light, near ultraviolet light, visible light, near infrared light, infrared light, and the like in the present specification are in accordance with the definitions described in "Iwanami Rtkagaku Jiten, 4th edition", compiled by R. Kubo et al (1987, Iwanami).

The polymerizable composition of the present invention can give an intended polymer product or cured product by applying thereto light energy from a light such as a low-pressure mercury lamp, an intermediate-pressure mercury lamp, a high-pressure mercurylamp, an ultrahigh-pressure mercury lamp, a xenon lamp, a carbon arc lamp, a metal halide lamp, a fluorescent lamp, a tungsten lamp, an argon ion laser, a helium neon laser, a krypton ion laser, a variety of laser diodes, a YAG laser, a light emission diode, a CRT light source or a plasma light source and/or heat energy by heating or from a thermal head.

Therefore, the polymerizable composition of the present invention can be used in the fields of photosensitive materials such as an ink, a form plate material, a photoresist, a direct printing material and a hologram material, recording media such as microcapsules, and others such as an adhesive and a sealing agent by applying it to a substrate together with a binder and the like.

The sulfonium or oxosulfonium complex of the formula (1) can be synthesized by reacting a sulfonium or oxosulfonium complex of the formula (2),

wherein $R^1$ is a benzyl group, a substituted benzyl group, a phenacyl group, a substituted phenacyl group, an aryloxy group, a substituted aryloxy group, an alkenyl group or a substituted alkenyl group, each of $R^2$ and $R^3$ is independently any one of groups defined as $R^1$, an alkyl group, a substituted alkyl group, an aryl group, a substituted aryl group, an aralkyl group, a substituted aralkyl group, an alkynyl group, a substituted alkynyl group, an alicyclic group, a substituted alicyclic group, an alkoxyl group, a substituted alkoxyl group, an alkylthio group, a substituted alkylthio group, an amino group or a substituted amino group, or $R^2$ and $R^3$ bond together forming a ring structure, $R^4$ is an oxygen atom or lone pair, X is a halogen atom, $BF_4$, $PF_6$, $SbF_6$, $AsF_6$, $ClO_4$, methylsulfuric acid, trifluoromethylsulfuric acid, benzenesulfonate or p-toluenesulfonate.
with an organic boron compound of the formula (3),

wherein M is an alkali metal, ammonium or hydrocarbon-substituted ammonium, each of $R^5$, $R^6$, $R^7$ and $R^8$ is independently an optionally substituted alkyl group, an optionally substituted aryl group, an optionally substituted aralkyl group, an optionally substituted alkenyl group or an optionally substituted alkynyl group, and at least two members of $R^5$, $R^6$, $R^7$ and $R^8$ may bond together forming a ring structure, provided that not all of $R^5$, $R^6$, $R^7$ and $R^8$ are optionally substituted aryls.
in a predetermined organic solvent, water, or a mixed solvent of an organic solvent and water.

The sulfonium complex and oxosulfonium complex used as raw materials in the present invention can be selected from sulfonium complexes and oxosulfonium complexes described in "Shin Jikken Kagaku Koza (New Experimental Chemistry Course)", Chemical Society of Japan, vol. 14, page 1,838 (1978, Maruzen Co., Ltd.), "Organic Sulfur Chemistry" (Synthesis Reaction), S. Ohac, page 237 (1982, Kagaku Dojin), "Sulfur Ylides", B. M. Trost and L. S. Melvin, Jr., page 6 (1975, Academic Press), Journal of Chemical Society, (C), page 682 (1970), etc. Journal of Japanese Chemical Society, Vol. 87, No. 5, page 456 (1966), Journal of Japanese Chemical Society, Vol. 87, No. 10, page 1,969 (1966), European Patent 35,969. The organic boron complex used as another raw material in the present invention can be selected from organic boron complexes described in Justus Liebigs Annalert der Chemic, vol. 563, page 110 (1949), Journal of Organic Chemistry, vol. 29, page 1,971 (1964), Journal of Chemical Society, Perkin 2, page 1,225 (1978), etc.

The solvent for the above synthesis is preferably determined on the basis of the solubility of the raw materials in the solvent and the properties of the sulfonium or oxosulfonium complex intended as a product.

For example, when the raw materials are water-soluble, it is preferred to use water as a solvent. Specifically, when the anion portion of the sulfonium or oxosulfonium complex as a raw material is composed of chlorine or bromine and when the cation portion of the boron compound as a raw material is an alkali metal, the sulfonium complex or oxosulfonium complex synthesized as a product can be easily obtained by a simple method in which the crystal formed in the reaction system was filtered, washed with water and dried, since the sulfonium complex or oxosulfonium complex as a product is hardly soluble in water.

Further, when the solvent used in the above reaction system contains an organic solvent having poor miscibility to water, such as dichloromethane, chloroform, ethyl acetate, benzene or ether, the sulfonium complex or oxosulfonium complex synthesized as a product can be extracted into the organic layer when formed. This method is suitable particularly for synthesizing an oily sulfonium or oxosulfonium complex which is unstable to water or is hardly crystallized. In this case, however, the organic solvent is required to dissolve the formed sulfonium or oxosulfonium complex.

When one of the raw materials has poor solubility in water, or more specifically, when the anion portion of the sulfonium or oxosulfonium complex as a raw material is composed of $BF_4$, $PF_6$, $SbF_6$, $AsF_6$, $ClO_4$, methylsulfuric acid, trifluormethylsulfuric acid, benzene sulfonate or p-toluenesulfonate or when the cation portion of the organic boron compound as a raw material is composed of quaternary ammonium, it is preferred to use an organic solvent having high solubility to the raw material or a mixed solvent containing wafer and the organic solvent. When the solvent in this case is selected from organic solvents miscible with water, such as lower alcohol, acetonitrile, acetone, tetrahydrofuran, dimethylformamide and dimethylsulfoxide, the sulfonium or oxosulfonium complex as a product can be easily recovered in the form of a crystal or an oily substance by adding an excess of water after the reaction finishes. The so-obtained sulfonium or oxosulfonium complex can be used directly for general purposes, and it may further be recrystallized from an organic solvent to obtain a sulfonium or oxosulfonium complex product having a higher purity.

The reaction temperature may be set at any temperature which is higher than the boiling point of a reaction solvent and lower than the temperature at which the formed sulfonium or oxosulfonium complex decomposes. Since, however, the above reaction method is free from the release and intake of a large amount of heat, and since the reaction proceeds readily around room temperature, it is preferred to carry out the reaction around room temperature in view of economic performance and safety.

The sulfonium or oxosulfonium complex of the present invention is useful as a catalyst for curing photo-curing and heat-curing compositions, and particularly useful as a catalyst for polymerizing and curing ethylenically unsaturated compounds. A sulfonium complex or an oxosulfonium complex is inherently unstable. However, when the anion portion of such a complex is replaced with boron on which an organic substituent such as an alkyl group, aryl group, or the like is substituted, then, the resultant complex shows improvement in crystallizability, stability and solubility in an organic solvent, and provides excellent sensitivity for the polymerization of ethylenically unsaturated compounds, as compared with any other conventional sulfonium complex.

The sulfonium or oxosulfonium complex of the formula (1) used in the composition of the present invention is considered to be excited by applying optical and/or heat energy and decomposed to generate free radicals. As a result, the above radical-polymerizable, ethylenically unsaturated compound can be polymerized.

The sulfonium and oxosulfonium complexes of the formula (1) generally have no absorption to light having a wavelength longer than the wavelength of ultraviolet light, and is scarcely active to light in a region of from visible light to near infrared light. However, when a fused polycyclic aromatic group such as naphthyl, anthranyl, phenathryl or anthryl or other proper substituent is introduced as any one of $R^1$ to $R^8$ except for $R^4$, or when a proper sensitizer which has been already detailed above is used in combination, the composition of the present invention acquires a very high sensitivity to light in a region of from near ultraviolet light to near infrared light.

Although being not clear in detail, the optical reaction mechanism of the composition of the present invention is considered as follows. When a sensitizer is used in combination, intermolecular electron transfer takes place between the sensitizer and the complex of the formula (1) as a polymerization initiator. When the complex of the formula (1) is used alone, intermolecular electron transfer or energy transfer takes place in the molecule of the complex. As a result, cleavage occurs in a site where the cation portion and anion portion bond to each other in the complex of the formula (1), and free radicals are generated. The generated free radicals cause the polymerization or crosslinking reaction of the above radical-polymerizable, ethylenically unsaturated compound.

Further, when proper substituents are selected as substituents on the sulfonium or oxosulfonium cation, the complex is improved in crystallizability, stability and solubility in a variety of organic solvents. Furthermore, when polymerized, the polymerizable composition containing such a complex and an ethylenically unsaturated compound shows much more improved sensitivity than a polymerizable composition containing any conventional sulfonium complex and an ethylenically unsaturated compound.

The sulfonium or oxosulfonium complex of the formula (1), provided by the present invention, is effective as a polymerization initiator for radical-polymerizable, ethylenically unsaturated compounds. A polymerizable composition containing the above complex and the above compound can be polymerized and cured by applying optical and/or heat energy.

The polymerizable composition of the present invention can give intended polymer products and cured products by applying thereto light energy from a light source such as a low-pressure mercury lamp, an intermediate-pressure mercury lamp, a high-pressure mercury lamp, an ultrahigh-pressure mercury lamp, a xenon lamp, a carbon arc lamp, a metal halide lamp, a fluorescent lamp, a tungsten lamp, an argon ion laser, a helium neon laser, a krypton ion laser, a variety of laser diodes, a YAG laser, a light emission diode, a CRT light source or a plasma light source and/or heat energy by heating or from a thermal head.

Therefore, the polymerizable composition of the present invention can be used as a printing material, a photoresist, an electron photography material, a direct printing material and a hologram material by applying it to a substrate together with a binder, etc., and it can be also used in a variety of recording media and adhesives by applying it as a core material for microcapsules.

The present invention will be explained more in detail by reference to Examples.

EXAMPLE 1

Synthesis of dimethylphenacylsulfonium-butyltriphenylborate

An aqueous solution of 5.424 g of lithium butyltriphenylborate in 100 ml of water was added to an aqueous solution of 5.090 g of dimethylphenacylsulfonium bromide in 200 ml of water, and the resultant mixture was stirred at room temperature for 30 minutes. The reaction mixture was filtered, and the resultant crystal was washed with water and dried to give 5.202 g of dimethylphenacylsulfonium-butyltriphenylborate as a white crystal.

Melting point 134°–137° C. (began to gradually decompose around 120° C.)

FIG. 1 shows the IR spectrum of the above complex.

FD-MS m/z 181 $((M-BC_4H_9(C_6H_5)_3)^+)$

Elemental analysis $C_{32}H_{37}BOS$

Calculated C: 79.99%, H: 7.76%

Found C: 80.01%, H: 7.69%

EXAMPLE 2

Synthesis of dimethylphenacyloxosulfonium-butyltriphenylborate

A solution of 7.91 g of tetrabutylammonium butyltriphenylborate in 100 ml of acetone was added to a solution of 5.00 g of dimethylphenacyloxosulfonium pentafluorophosphate in 100 ml of acetone, and the resultant mixture was stirred at room temperature for 30 minutes. Then, 200 ml of water was added to form a yellow oily precipitate. The precipitate was separated and recovered, and 100 ml of dichloromethane was added. The resultant dichloromethane layer was washed with water, dried and concentrated to give 2.46 g of dimethylphenacyloxosulfonium-butyltriphenylborate as a white crystal.

Melting point 153°–156° C.

IR (KBr) $cm^{-1}$ 3054, 2843, 1678, 1038, 741, 713

FD-MS m/z 197 $((M-BC_4H_9(C_6H_5)_3)^+)$

Elemental analysis $C_{32}H_{37}BO_2S$

Calculated C: 77.41%, H: 7.51%

Found C: 77.52%, H: 7.38%

EXAMPLE 3

Synthesis of dimethylbenzylsulfonium-butyltriphenylborate

An aqueous solution of 10.11 g of lithium butyltriphenylborate in 100 ml of water was added to an aqueous solution of 6.24 g of dimethylphenacylsulfonium chloride in 150 ml of water, and the resultant mixture was stirred at room temperature for 30 minutes. The reaction mixture was filtered, and the resultant crystal was washed with water and dried to give 13.58 g of dimethylbenzylsulfonium-butyltriphenylborate as a white crystal.

Melting point 131°–134° C.

IR (KBr) $cm^{-1}$ 3053, 2845, 740, 712

FD-MS m/z 153 $((M-BC_4H_9(C_6H_5)_3)^+)$

Elemental analysis $C_{31}H_{37}BS$

Calculated C: 82.28%, H: 8.24%

Found C: 82.39%, H: 8.31%

EXAMPLE 4

Synthesis of dimethylbenzyloxosulfonium-butyltriphenylborate

An aqueous solution of 8.90 g of lithium butyltriphenylborate in 100 ml of water was added to a solution of 7.24 g of dimethylphenacyloxosulfonium bromide in 100 ml of methanol, and the resultant mixture was stirred at room temperature for 30 minutes. Then, the reaction mixture was filtered, and the resultant crystal was washed with water and dried to give 10.61 g of dimethylbenzyloxosulfonium-butyltriphenylborate as a white crystal.

Melting point 145°–148° C.

IR (KBr) cm$^{-1}$ 3053, 2842, 1040, 740, 714

FD-MS m/z 169 ((M-BC$_4$H$_9$(C$_6$H$_5$)$_3$)$^+$)

Elemental analysis C$_{31}$H$_{37}$BS

Calculated C: 79.47%, H: 7.96%

Found C: 79.52%, H: 8.04%

EXAMPLE 5

Synthesis of dimethyl-p-chlorophenacylsulfonium-butyltriphenylborate

An aqueous solution of 6.10 g of lithium butyltriphenylborate in 100 ml of water was added to a solution of 5.00 g of dimethyl-p-chlorophenacylsulfonium chloride in 100 ml of water, and the resultant mixture was stirred at room temperature for 30 minutes. Then, the reaction mixture was filtered, and the resultant crystal was washed with water and dried to give 9.34 g of dimethyl-p-chlorophenacylsulfonium-butyltriphenylborate as a white crystal.

FD-MS m/z 215 ((M-BC$_4$H$_9$(C$_6$H$_5$)$_3$)$^+$)

Elemental analysis C$_{32}$H$_{36}$BClOS

Calculated C: 74.64%, H: 7.05%

Found C: 74.59%, H: 7.12 7%

EXAMPLE 6

Synthesis of dimethyl-p-methoxylphenylsulfonium-butyltriphenylborate

An aqueous solution of 5.26 g of lithium butyltriphenylborate in 100 ml of water was added to an aqueous solution of 5.00 g of dimethyl-p-methoxyphenacylsulfonium bromide in 100 ml of water, and the resultant mixture was stirred at room temperature for 30 minutes. Then, the reaction mixture was filtered, and the resultant crystal was washed with water and dried to give 7.64 g of dimethyl-p-methoxyphenacylsulfonium-butyltriphenylborate as a white crystal.

FD-MS m/z 211 ((M-BC$_4$H$_9$(C$_6$H$_5$)$_3$)$^+$)

Elemental analysis C$_{33}$H$_{39}$BO$_2$S

Calculated C: 77.64%, H: 7.70%

Found C: 77.59%, H: 7.74%

EXAMPLE 7

Synthesis of dimethyl-p-chlorobenzylsulfonium-butyltriphenylborate

An aqueous solution of 11.27 g of lithium butyltriphenylborate in 200 ml of water was added to an aqueous solution of 8.21 g of dimethyl-p-chlorobenzylsulfonium chloride in 200 ml of water, and the resultant mixture was stirred at room temperature for 30 minutes. Then, the reaction mixture was filtered, and the resultant crystal was washed with water and dried to give 16.67 g of dimethyl-p-chlorobenzylsulfonium-butyltriphenylborate as a white crystal.

FD-MS m/z 187 ((M-BC$_4$H$_9$(C$_6$H$_5$)$_3$)$^+$)

Elemental analysis C$_{31}$H$_{36}$BClS

Calculated C: 76.46%, H: 7.45%

Found C: 76.54%, H: 7.39%

EXAMPLE 8

Synthesis of dimethyl-p-cyanobenzylsulfonium-butyltriphenylborate

An aqueous solution of 4.98 g of lithium butyltriphenylborate in 100 ml of water was added to an aqueous solution of 4.20 g of dimethyl-p-cyanobenzylsulfonium bromide in 100 ml of water, and the resultant mixture was stirred at room temperature for 30 minutes. Then, the reaction mixture was filtered, and the resultant crystal was washed with water and dried to give 6.59 g of dimethyl-p-cyanobenzylsulfonium-butyltriphenylborate as a white crystal.

FD-MS m/z 178 ((M-BC$_4$H$_9$(C$_6$H$_5$)$_3$)$^+$)

Elemental analysis C$_{32}$H$_{36}$BNS

Calculated C: 80.49%, H: 7.60%, N: 2.93%

Found C: 80.32%, H: 7.45%, N:2.97%

EXAMPLE 9

Synthesis of di-tert-butylphenacylsulfonium-butyltriphenylborate

An aqueous solution of 5.59 g of lithium butyltriphenylborate in 100 ml of water was added to an aqueous solution of 6.30 g of di-tert-butylphenacylsulfonium bromide in 150 ml of water, and the resultant mixture was stirred at room temperature for 30 minutes. Then, the reaction mixture was filtered, and the resultant crystal was washed with water and dried to give 8.98 g of di-tert-butylphenacylsulfonium-butyltriphenylborate as a white crystal.

FD-MS m/z 265 ((M-BC$_4$H$_9$(C$_6$H$_5$)$_3$)$^+$)

Elemental analysis C$_{38}$H$_{49}$BOS

Calculated C: 80.83%, H: 8.75%

Found C: 80.72%, H: 8.64%

EXAMPLE 10

Synthesis of didodecylphenacylsulfonium-butyltriphenylborate

A mixture of 7.20 g of didodecylphenacylsulfonium bromide and 3.87 g of lithium butyltriphenylborate was stirred in 200 ml of ethanol at room temperature for 30 minutes. The reaction mixture was poured into 1,000 ml of water, and the resultant oily component was separated, recovered, washed with water and dried to give 6.78 g of didodecylphenacylsulfonium-butyltriphenylborate.

FD-MS m/z 489 ((M-BC$_4$H$_9$(C$_6$H$_5$)$_3$)$^+$)

Elemental analysis C$_{54}$H$_{81}$BOS

Calculated C: 82.19%, H: 10.35%

Found C: 82.12%, H: 10.27%

EXAMPLE 11

Synthesis of di-tert-butylbenzylsulfonium-butyltriphenylborate

An aqueous solution of 4.83 g of lithium butyltriphenylborate in 100 ml of water was added to an aqueous solution of 5.00 g of di-tert-butylbenzylsulfonium bromide in 200 ml of water, and the resultant mixture was stirred at room temperature for 30 minutes. Then, the reaction mixture was filtered, and the resultant crystal was washed with water and dried to give 5.90 g of di-tert-butylbenzylsulfonium-butyltriphenylborate as a white crystal.

FD-MS m/z 237 $((M-BC_4H_9(C_6H_5)_3)^+)$
Elemental analysis $C_{37}H_{49}BS$
Calculated C: 82.81%, H: 9.20%
Found C: 82.91%, H: 9.42%

EXAMPLE 12

Synthesis of didodecylbenzylsulfonium-butyltriphenylborate

A mixture of 6.30 g of didodecylbenzylsulfonium bromide and 3.56 g of lithium butyltriphenylborate was stirred in 200 ml of ethanol at room temperature for 30 minutes. The reaction mixture was poured into 1,000 ml of water, and the resultant oily component was separated, recovered, washed with water and dried to give 5.66 g of dodecylbenzylsulfonium-butyltriphenylborate.

FD-MS m/z 461 $((M-BC_4H_9(C_6H_5)_3)^+)$
Elemental analysis $C_{53}H_{81}BS$
Calculated C: 83.64%, H: 10.73%
Found C: 83.72%, H: 10.82%

EXAMPLE 13

Synthesis of dimethylphenacylsulfonium-butyltrimesitylborate

An aqueous solution of 4.14 g of lithium butyltrimesitylborate in 100 ml of water was added to an aqueous solution of 2.50 g of dimethylphenacylsulfonium bromide in 100 ml of water, and the resultant mixture was stirred at room temperature for 30 minutes. Then, the reaction mixture was filtered, and the resultant crystal was washed with water and dried to give 4.19 g of dimethylphenacylsulfonium-butyltrimesityllborate.

FD-MS m/z 181 $((M-BC_4H_9(C_6H_2(CH_3)_3)_3)^+)$
Elemental analysis $C_{41}H_{55}BOS$
Calculated C: 81.16%, H: 9.14%
Found C: 81.06%, H: 9.07%

EXAMPLE 14

Synthesis of dimethylphenacylsulfonium-tert-butyltriethylborate

An aqueous solution of 3.10 g of lithium tert-butyltriethylborate in 100 ml of water was added to an aqueous solution of 5.00 g of dimethylphenacylsulfonium bromide in 200 ml of water, and the resultant mixture was stirred at room temperature for 30 minutes. Then, the reaction mixture was filtered, and the resultant crystal was washed with water and dried to give 5.54 g of dimethylphenacylsulfonium-tert-butyltriethylborate as a white crystal.

FD-MS m/z 181 $((M-BC_4H_9(C_2H_5)_3)^+)$
Elemental analysis $C_{20}H_{37}BOS$
Calculated C: 71.41%, H: 11.09%
Found C: 71.52%, H: 10.99%

EXAMPLE 15

Synthesis of dimethylphenacylsulfonium-phenyltriethylborate

An aqueous solution of 3.49 g of lithium phenyltriethylborate in 100 ml of water was added to an aqueous solution of 5.00 g of dimethylphenacylsulfonium bromide in 200 ml of water, and the resultant mixture was stirred at room temperature for 30 minutes. Then, the reaction mixture was filtered, and the resultant crystal was washed with water and dried to give 5.58 g of dimethylphenacylsulfonium-phenyltriethylborate.

FD-MS m/z 181 $((M-BC_6H_5(C_2H_5)_3)^+)$
Elemental analysis $C_{22}H_{33}BOS$
Calculated C: 74.15%, H: 9.33%
Found C: 74.02%, H: 9.42%

EXAMPLE 16

Synthesis of dimethylphenacylsulfonium-benzyltriphenylborate

An aqueous solution of 6.51 g of lithium benzyltriphenylborate in 100 ml of water was added to an aqueous solution of 5.00 g of dimethylphenacylsulfonium bromide in 200 ml of water, and the resultant mixture was stirred at room temperature for 30 minutes. Then, the reaction mixture was filtered, and the resultant crystal was washed with water and dried to give 8.09 g of dimethylphenacylsulfonium-benzyltriphenylborate.

FD-MS m/z 181 $((M-BCH_2C_6H_5(C_6H_5)_3)^+)$
Elemental analysis $C_{35}H_{35}BOS$
Calculated C: 81.70%, H: 6.86%
Found C: 81.62%, H: 6.79%

EXAMPLE 17

Synthesis of dimethylphenacylsulfonium-butyltrimethoxyphenylborate

An aqueous solution of 3.03 g of lithium butyltrimethoxyphenylborate in 50 ml of water was added to an aqueous solution of 2.00 g of dimethylphenacylsulfonium bromide in 50 ml of water, and the resultant mixture was stirred at room temperature for 30 minutes. Then, the reaction mixture was filtered, and the resultant crystal was washed with water and dried to give 3.15 g of dimethylphenacylsulfonium-butyltrimethoxyphenylborate.

FD-MS m/z 181 $((M-BC_4H_9(C_6H_4OCH_3)_3)^+)$
Elemental analysis $C_{35}H_{43}BO_4S$
Calculated C: 73.67%, H: 7.60%
Found C: 73.54%, H: 7.53%

EXAMPLE 18

Synthesis of dimethylphenacylsulfonium-vinyltriphenylborate

An aqueous solution of 2.11 g of lithium vinyltriphenylborate in 100 ml of water was added to an aqueous solution of 2.00 g of dimethylphenacylsulfonium bromide in 50 ml of water, and the resultant mixture was stirred at room temperature for 30 minutes. Then, the reaction mixture was filtered, and the resultant crystal was washed with water and dried to give 2.69 g of dimethylphenacylsulfonium-vinyltriphenylborate.

FD-MS m/z 181 ((M-BC$_2$H$_3$(C$_6$H$_5$)$_3$)$^+$)
Elemental analysis C$_{30}$H$_{31}$BOS
Calculated C: 79.99%, H: 6.94%
Found C: 80.05%, H: 7.01%

EXAMPLE 19

Synthesis of dimethylphenacylsulfonium-ethynyltriphenylborate

An aqueous solution of 2.22 g of lithium ethynyltriphenylborate in 100 ml of water was added to an aqueous solution of 2.00 g of dimethylphenacylsulfonium bromide in 50 ml of water, and the resultant mixture was stirred at room temperature for 30 minutes. Then, the reaction mixture was filtered, and the resultant crystal was washed with water and dried to give 2.20 g of dimethylphenacylsulfonium-ethynyl triphenylborate as a white crystal.

FD-MS m/z 181 ( (M-BC$_2$H(C$_6$H$_5$)$_3$)$^+$)
Elemental analysis C$_{30}$H$_{29}$BOS
Calculated C: 80.35%, H: 6.52%
Found C: 80.39%, H: 6.48%

EXAMPLE 20

Synthesis of dimethylphenacylsulfonium-butyltris(p-fluorophenyl)borate

An aqueous solution of 2.76 g of lithium butyltris(p-fluorophenyl)borate in 100 ml of water was added to an aqueous solution of 2.00 g of dimethylphenacylsulfonium bromide in 50 ml of water, and the resultant mixture was stirred at room temperature for 30 minutes. Then, the reaction mixture was filtered, and the resultant crystal was washed with water and dried to give 2.90 g of dimethylphenacylsulfonium-butyltris(p-fluorophenyl)borate as a white crystal.

FD-MS m/z 181 ((M-BC$_4$H$_9$(C$_6$H$_4$F)$_3$)$^+$)
Elemental analysis C$_{32}$H$_{34}$BF$_3$OS
Calculated C: 71.91%, H: 6.41%
Found C: 72.00%, H: 6.49%

EXAMPLE 21

Synthesis of dimethylphenacylsulfonium-butyltris[3,5-bis(trifluoromethyl)phenyl]borate A solution of 5,47 g of lithium butyltris[3,5-bis(trifluoromethyl)phenyl] borate in 100 ml of acetone was added to a solution of 2.00 g of dimethylphenacylsulfonium bromide in 100 ml of methanol, and the resultant mixture was stirred at room temperature for 30 minutes. The reaction mixture was poured into 500 ml of water, and the resultant oily component was separated, recovered, washed with water and dried to give 4.35 g of dimethylphenacylsulfonium-butyltris[ 3,5-bis(trifluoromethyl)phenylborate.

FD-MS m/z 181 ((M-BC$_4$H$_9$(C$_6$H$_3$(CF$_3$)$_2$)$_3$)$^+$)
Elemental analysis C$_{38}$H$_{31}$BF$_{18}$OS
Calculated C: 51.37%, H: 3.52%
Found C: 51.42%, H: 3.49%

EXAMPLE 22

Synthesis of trimethylsulfonium-butyltriphenylborate

An aqueous solution of 7.50 g of lithium butyltriphenylborate in 100 ml of water was added to an aqueous solution of 5.00 g of trimethylsulfonium iodide in 200 ml of water, and the resultant mixture was stirred at room temperature for 30 minutes. Then, the reaction mixture was filtered, and the resultant crystal was washed with water and dried to give 8.02 g of trimethyloxosulfonium-butyltriyphenylborate.

FD-MS m/z 77 ((M-BC$_4$H$_9$(C$_6$H$_5$)$_3$)$^+$)
Elemental analysis C$_{25}$H$_{33}$BS
Calculated C: 79.77%, H: 8.84%
Found C: 79.86%, H: 8.76%

EXAMPLE 23

Synthesis of trimethyloxosulfonium-butyltriphenylborate

An aqueous solution of 6.95 g of lithium butyltriphenylborate in 100 ml of water was added to an aqueous solution of 5.00 g of trimethyloxosulfonium iodide in 200 ml of water, and the resultant mixture was stirred at room temperature for 30 minutes. Then, the reaction mixture was filtered, and the resultant crystal was washed with water and dried to give 5.60 g of trimethyloxosulfonium-butyl triyphenylborate.

FD-MS m/z 93 ((M-BC$_4$H$_9$(C$_6$H$_5$)$_3$)$^+$)
Elemental analysis C$_{25}$H$_{33}$BOS
Calculated C: 76.52%, H: 8.48%,
Found C: 76.59%, H: 8.53%,

EXAMPLE 24

Synthesis of tetramethylenephenacylsulfonium-butyltriphenylborate

An aqueous solution of 5.00 g of lithium butyltriphenylborate in 100 ml of water was added to an aqueous solution of 4.69 g of tetramethylenephenacylsulfonium bromide in 200 ml of water, and the resultant mixture was stirred at room temperature for 30 minutes. Then, the reaction mixture was filtered, and the resultant crystal was washed with water and dried to give 7.65 g of tetramethylenephenacylsulfonium-butyltriphenylborate.

FD-MS m/z 207 ((M-BC$_4$H$_9$(C$_6$H$_5$)$_3$)$^+$)
Elemental analysis C$_{34}$H$_{39}$BOS
Calculated C: 80.62%, H: 7.76%,
Found C: 80.53%, H: 7.67%,

EXAMPLE 25

Synthesis of tetramethylenebenzylsulfonium-butyltriphenylborate

An aqueous solution of 5.00 g of lithium butyltriphenylborate in 100 ml of water was added to an aqueous solution of 4.23 g of tetramethylencbenzylsulfonium bromide in 200 ml of water, and the resultant mixture was stirred at room temperature for 30 minutes. Then, the reaction mixture was filtered, and the resultant crystal was washed with water and dried to give 7.23 g of tetramethylencbenzylsulfonium-butyltriphenylborate.

FD-MS m/z 179 ( $(M-BC_4H_9(C_6H_5)_3)^+$)
Elemental analysis $C_{33}H_{39}BS$
Calculated C: 82.83%, H: 8.22%
Found C: 82.79%, H: 8.16%

EXAMPLE 26

Synthesis of dimethylallylsulfonium-butyltriphenylborate

An aqueous solution of 5.00 g of lithium butyltriphenylborate in 100 ml of water was added to an aqueous solution of 2.99 g of dimethylallylsulfonium bromide in 200 ml of water, and the resultant mixture was stirred at room temperature for 30 minutes. Then, the reaction mixture was filtered, and the resultant crystal was washed with water and dried to give 6.14 g of dimethylallylsulfonium-butyltriphenylborate.

FD-MS m/z 103 ( $(M-BC_4H_9(C_6H_5)_3)^+$)
Elemental analysis $C_{27}H_{35}BS$
Calculated C: 80.58%, H: 8.77%
Found C: 80.39%, H: 8.59%

EXAMPLE 27

Synthesis of dibutylallylsulfonium-butyltriphenylborate

An aqueous solution of 5.00 g of lithium butyltriphenylborate in 100 ml of water was added to an aqueous solution of 4.36 g of dibutylallylsulfonium bromide in 200 ml of water, and the resultant mixture was stirred at room temperature for 30 minutes. Then, the reaction mixture was filtered, and the resultant crystal was washed with water and dried to give 6.97 g of dibutylallylsulfonium-butyltriphenylborate.

FD-MS m/z 187 $((M-BC_4H_9(C_6H_5)_3)^+)$
Elemental analysis $C_{33}H_{47}BS$
Calculated C: 81.45%, H: 9.74%
Found C: 81.37%, H: 9.82%

EXAMPLE 28

Synthesis of dimethylcyanomethylsulfonium-butyltriphenylborate

An aqueous solution of 5.00 g of lithium butyltriphenylborate in 100 ml of water was added to an aqueous solution of 3.74 g of dimethylcyanomethylsulfonium iodide in 200 ml of water, and the resultant mixture was stirred at room temperature for 30 minutes. Then, the reaction mixture was filtered, and the resultant crystal was washed with water and dried to give 4.48 g of dimethylcyanomethylsulfonium-butyltriphenylborate.

FD-MS m/z 102 $((M-BC_4H_9(C_6H_5)_3)^+)$
Elemental analysis $C_{26}H_{32}BSN$
Calculated C: 77.80%, H: 8.04%, N: 3.49%
Found C: 77.72%, H: 7.98%, N: 3.37%

EXAMPLE 29

Synthesis of dimethylacetylmethylsulfonium-butyltriphenylborate

An aqueous solution of 5.00 g of lithium butyltriphenylborate in 100 ml of water was added to an aqueous solution of 3.25 g of dimethylacetylmethylsulfonium bromide in 200 ml of water, and the resultant mixture was stirred at room temperature for 30 minutes. Then, the reaction mixture was filtered, and the resultant crystal was washed with water and dried to give 5.69 g of dimethylacetylmethylsulfonium-butyltriphenylborate.

FD-MS m/z 119 $((M-BC_4H_9(C_6H_5)_3)^+)$
Elemental analysis $C_{27}H_{35}BOS$
Calculated C: 77.50%, H: 8.43%
Found C: 77.57%, H: 8.49%

EXAMPLE 30

Synthesis of dimethylethoxycarbonylmethylsulfonium-butyltriphenylborate

An aqueous solution of 5.00 g of lithium butyltriphenylborate in 100 ml of water was added to an aqueous solution of 3.74 g of dimethylethoxycarbonylmethylsulfonium bromide in 200 ml of water, and the resultant mixture was stirred at room temperature for 30 minutes. Then, the reaction mixture was filtered, and the resultant crystal was washed with water and dried to give 6.32 g of dimethylethoxycarbonylmethylsulfonium-butyltriphenylborate.

FD-MS m/z 149 $((M-BC_4H_9(C_6H_5)_3)^+)$
Elemental analysis $C_{28}H_{37}BO_2S$
Calculated C: 74.99%, H: 8.32%
Found C: 75.07%, H: 8.27%

EXAMPLE 31

Synthesis of dimethyl(2-ethoxycarbonyl)isoprpylsulfonium-butyltriphenylborate

An aqueous solution of 5.00 g of lithium butyltriphenylborate in 100 ml of water was added to an aqueous solution of 4.20 g of dimethyl(2-ethoxyearbonyl)isopropylsulfonium bromide in 200 ml of water, and the resultant mixture was stirred at room temperature for 30 minutes. Then, the reaction mixture was filtered, and the resultant crystal was washed with water and dried to give 6.41 g of dimethyl (2-ethoxycarbonyl)isopropylsulfonium-butyltriphenylborate.

FD-MS m/z 177 $((M-BC_4H_9(C_6H_5)_3)^+)$
Elemental analysis $C_{30}H_{41}BO_2S$
Calculated C: 75.62%, H: 8.67%
Found C: 75.49%, H: 8.77%

EXAMPLE 32

Synthesis of dimethyl(N,N-dimethylaminocarbonyl)-cyanomethylsulfonium-butyltriphenylborate An aqueous solution of 5.00 g of lithium butyltriphenylborate in 100 ml of water was added to an aqueous solution of 4.13 g of dimethyl(N,N-dimethylaminocarbonyl)caynomethylsulfonium bromide in 200 ml of water, and the resultant mixture was stirred at room temperature for 30 minutes. Then, the reaction mixture was filtered, and the resultant crystal was washed with water and dried to give 4.74 g of dimethyl(N,N-dimethylaminocarbonyl)cyanomethylsulfoniumbutyltriphenylborate.

FD-MS m/z 173 $((M-BC_4H_9(C_6H_5)_3)^+)$

Elemental analysis $C_{29}H_{37}N_2OS$

Calculated C: 73.72%, H: 7.89%, N: 5.93%

Found C: 73.78%, H: 7.93%, N: 5.91%

EXAMPLE 33

Synthesis of dimethylmethylthiomethylsulfonium-butyltriphenylborate

An aqueous solution of 5.00 g of lithium butyltriphenylborate in 100 ml of water was added to an aqueous solution of 4.08 g of dimethymethyl thiomethylsulfonium iodide in 200 ml of water, and the resultant mixture was stirred at room temperature for 30 minutes. Then, the reaction mixture was filtered, and the resultant crystal was washed with water and dried to give 4.96 g of dimethylmethylthiomethylsulfonium-butyltriphenylborate.

FD-MS m/z 123 $((M-BC_4H_9(C_6H_5)_3)^+)$

Elemental analysis $C_{26}H_{35}BS_2$

Calculated C: 73.91%, H: 8.35%

Found C: 73.84%, H: 8.27%

EXAMPLE 34

Synthesis of dibenzylphenacylsulfonium-butyltriphenylborate

A solution of 3.00 g of lithium butyltriphenylborate in 100 ml of acetonitrile was added to a solution of 4.12 g of dibenzylphenacylsulfonium tetrafluoroborate in 100 ml of acetonitrile, and the resultant mixture was stirred at room temperature for 30 minutes. The reaction mixture was poured into 500 ml of water, and the resultant oily component was separated, recovered, washed with water and recrystallized from dichloromethane/ether to give 2.11 g of dibenzylphenacylsulfonium-butyltriphenylborate.

FD-MS m/z 333 $((M-BC_4H_9(C_6H_5)_3)^+)$

Elemental analysis $C_{44}H_{45}BOS$

Calculated C: 83.53%, H: 7.17%

Found C: 83.47%, H: 7.21%

EXAMPLE 35

Synthesis of diallylphenacylsulfonium-butyltriphenylborate

A solution of 3.00 g of lithium butyl triphenylborate in 100 ml of acetonitrile was added to a solution of 3.14 g of diallylphenacylsulfonium tetrafluoroborate in 100 ml of acetonitrile, and the resultant mixture was stirred at room temperature for 30 minutes. The reaction mixture was poured into 500 ml of water, and the resultant oily component was separated, recovered, washed with water and recrystallized from dichloromethane/ether to give 2.20 g of dialylphenacylsulfonium-butyltriphenylborate.

FD-MS m/z 233 $((M-BC_4H_9(C_6H_5)_3)^+)$

Elemental analysis $C_{36}H_{41}BOS$

Calculated C: 81.19%, H: 7.76%

Found C: 81.27%, H: 7.81%

EXAMPLE 36

Synthesis of dimethylvinylsulfonium-butyltriphenylborate

A solution of 3.00 g of lithium butyltriphenylborate in 100 ml of acetonitrile was added to a solution of 1.73 g of dimethylvinylsulfonium tetrafluoroborate in 100 ml of acetonitrile, and the resultant mixture was stirred at room temperature for 30 minutes. The reaction mixture was poured into 500 ml of water, and the resultant oily component was separated, recovered, washed with water and recrystallized from dichloromethane/ether to give 1.19 g of dimethylvinylsulfonium-butyltriphenylborate.

FD-MS m/z 89 $((M-BC_4H_9(C_6H_5)_3)^+)$

Elemental analysis $C_{26}H_{33}BS$

Calculated C: 80.40%, H: 8.56%

Found C: 80.28%, H: 8.51%

EXAMPLE 37

Synthesis of dimethylphenoxyoxosulfonium-butyltriphenylborate

A solution of 3.00 g of lithium butyltriphenylborate in 100 ml of acetonitrile was added to a solution of 3.10 g of dimethylphenoxyoxosulfonium bexafluorophosphate in 100 ml of acetone, and the resultant mixture was stirred at room temperature for 30 minutes. The reaction mixture was poured into 500 ml of water, and the resultant oily component was separated, recovered, washed with water and recrystallized from dichloromethane/ether to give 1.50 g of dimethylphenoxyoxosulfonium-butyltriphenylborate.

FD-MS m/z 171 $((M-BC_4H_9(C_6H_5)_3)^+)$

Elemental analysis $C_{30}H_{35}BO_2S$

Calculated C: 76.59%, H: 7.50%

Found C: 76.66%, H: 7.61%

EXAMPLE 38

Synthesis of tetramethylene-tert-butoxysulfonium-butyltriphenylborate

A solution of 3.00 g of lithium butyltriphenylborate in 100 ml of acetonitrile was added to a solution of 4.86 g of tetramethylene-tert-butoxysulfonium hexachloroantimonate in 100 ml of acetonitrile, and the resultant mixture was stirred at room temperature for 30 minutes. The reaction mixture was poured into 500 ml of water, and the resultant oily component was separated, recovered, washed with water and recrystallized from dichloromethane/ether to give 1.54 g of tetramethylene-tert-butoxysulfonium-butyltriphenylborate.

FD-MS m/z 161 $((M-BC_4H_9(C_6H_5)_3)^+)$

Elemental analysis $C_{30}H_{41}BOS$

Calculated C: 78.24%, H: 8.97%
Found C: 78.17%, H: 9.01%.

EXAMPLE 39

Synthesis of
dimethyl-p-tolylsulfonium-butyltriphenylborate

A solution of 3.00 g of lithium butyltriphenylborate in 100 ml of acetonitrile was added to a solution of 2.79 g of dimethyl-p-tolylsulfonium perchlorate in 100 ml of acetonitrile, and the resultant mixture was stirred at room temperature for minutes. The reaction mixture was poured into 500 ml of water, and the resultant oily component was separated, recovered, washed with water and recrystallized from dichloromethane/ether to give 1.70 g of dimethyl-p-tolylsulfonium-butyltriphenylborate.

FD-MS m/z 185 $((M-BC_4H_9(C_6H_5)_3)^+)$

Elemental analysis $C_{31}H_{37}BS_2$

Calculated C: 76.84%, H: 7.70%

Found C: 76.72%, H: 7.75%

EXAMPLE 40

Synthesis of
diethylethylthiosulfonium-butyltriphenylborate

A solution of 3.00 g of lithium butyl triphenylborate in 100 ml of acetonitrile was added to a solution of 7.19 g of diethylethylthiosulfonium triiodomercurate in 100 ml of acetonitrile, and the resultant mixture was stirred at room temperature for 30 minutes. The reaction mixture was poured into 500 ml of water, and the resultant oily component was separated, recovered, washed with water and recrystallized from dichloromethane/ether to give 1.21 g of diethylethylthiosulfonium-butyltriphenyl borate.

FD-MS m/z 151 $((M-BC_4H_9(C_6H_5)_3)^+)$

Elemental analysis $C_{28}H_{39}BS_2$

Calculated C: 74.64%, H: 8.73%

Found C: 74.54%, H: 8.69%

EXAMPLE 41

Synthesis of
di-tert-butyl-N-cyclohexylaminosulfonium-
butyltriphenylborate

A solution of 3.00 g of lithium butyltriphenylborate in 100 ml of acetonitrile was added to a solution of 2.75 g of di-tert-butyl-N-cyclohexylaminosulfonium chloride in 100 ml of methanol, and the resultant mixture was stirred at room temperature for 30 minutes. The reaction mixture was poured into 500 ml of water, and the resultant oily component was separated, recovered, washed with water and recrystallized from dichloromethane/ether to give 2.52 g of di-tert-butyl-N-cyclohexylaminosulfonium-butyltriphenylborate.

FD-MS m/z 244 $((M-BC_4H_9(C_6H_5)_3)^+)$

Elemental analysis $C_{36}H_{54}BNS$

Calculated C: 79.53%, H: 10.01%, N: 2.58%

Found C: 79.47%, H: 9.97%, N: 2.62%

EXAMPLE 42

Synthesis of
dimethyl-N-phenylaminosulfonium-butyltriphenylborate

A solution of 3.00 g of lithium butyltriphenylborate in 100 ml of acetonitrile was added to a solution of 1.86 g of dimethyl-N-phenylaminosulfonium chloride in 100 ml of methanol, and the resultant mixture was stirred at room temperature for 30 minutes. The reaction mixture was poured into 500 ml of water, and the resultant oily component was separated, recovered, washed with water and recrystallized from dichloromethane/ether to give 2.01 g of dimethyl-N-phenylaminosulfonium-butyltriphenylborate.

FD-MS m/z 154 $((M-BC_4H_9(C_6H_5)_3)^+)$

Elemental analysis $C_{30}H_{36}BNS$

Calculated C: 79.46%, H: 8.00%, N: 3.09%

Found C: 79.27%, H: 7.97%, N: 3.14%

EXAMPLE 43

Synthesis of
p-acetoxyphenylbenzylmethylsulfonium-
butyltriphenylborate

A solution of 3.00 g of lithium butyltriphenylborate in 100 ml of acetonitrile was added to a solution of 4.99 g of p-acetoxyphenylbenzylsulfonium hexafluoroantimonate in 100 ml of acetonitrile, and the resultant mixture was stirred at room temperature for 30 minutes. The reaction mixture was poured into 500 ml of water, and the resultant oily component was separated, recovered, washed with water and recrystallized from dichloromethane/ether to give 1.81 g of p-acetoxyphenylbenzylmethylsulfonium-butyltriphenylborate.

FD-MS m/z 273 $((M-BC_4H_9(C_6H_5)_3)^+)$

Elemental analysis $C_{38}H_{41}BO_2S$

Calculated C: 79.71%, H: 7.22%

Found C: 79.83%, H: 7.17%

EXAMPLE 44

Synthesis of
p-methoxycarbonyloxyphenylbenzylmethylsulfonium-
butyltriphenylborate A solution of 3.00 g of lithium butyl triphenylborate in 100 ml of acetonitrile was added to a solution of 5.15 g of p-methoxycarbonyloxyphenylbenzylmethylsulfonium hexafluoroantimonate in 100 ml of acetonitrile, and the resultant mixture was stirred at room temperature for 30 minutes. The reaction mixture was poured into 500 ml of water, and the resultant oily component was separated, recovered, washed with water and recrystallized from dichloromethane/ether to give 1.84 g of p-methoxycarbonyloxyphenylbenzylmethylsulfoniumbutyltriphenylborate.

FD-MS m/z 289 $((M-BC_4H_9(C_6H_5)_3)^+)$

Elemental analysis $C_{38}H_{41}BO_3S$

Calculated C: 77.54%, H: 7.02%

Found C: 77.46%, H: 6.99%

EXAMPLE 45

Synthesis of phenylmethyl(2-phenyl-3,3-dicyanopropen-2-yl) sulfonium-butyltriphenylborate A solution of 2.50 g of lithium butyltriphenylborate in 100 ml of acetonitrile was added to a solution of 3.09 g of phenylmethyl(2-phenyl-3,3-dicyanopropene-2-yl)sulfonium tetrafluoroborate in 100 ml of dichloromethane, and the resultant mixture was stirred at room temperature for 2 hours. The reaction mixture was poured into 500 ml of water, and the dichloromethane layer was separated, recovered, washed with water and recrystallized from dichloromethane/ether to give 0.93 g of phenylmethyl(2-phenyl-3,3-dicyanopropene-2-yl)sulfonium-butyltriphenylborate.

FD-MS m/z 291 ((M-BC$_4$H$_9$(C$_6$H$_5$)$_3$)$^+$)
Elemental analysis C$_{40}$H$_{39}$BN$_2$S
Calculated C: 81.34%, H: 6.66%, N: 4.74%
Found C: 81.21%, H: 6.72%, N: 4.69%.

EXAMPLE 46

Synthesis of diphenylphenacylsulfonium-n-butyltriphenylborate

A solution of 5.03 g of lithium n-butyltriphenylborate in 50 ml of acetonitrile was added to a solution of 6.65 g of diphenylphenacylsulfonium perchlorate in 100 ml of acetonitrile, and the resultant mixture was stirred at room temperature for 30 minutes. Then, 200 ml of water was added. The resultant precipitate of a yellow oily component was recovered, and 100 ml of dichloromethane was added. The dichloromethane layer was washed with water, dried and concentrated to give 3.67 of diphenylphenacylsulfonium-n-butyltriphenylborate. Melting point: 121–124 (gradually melted around 110° C.).

FD-MS m/z 305 ((M-B(C$_4$H$_9$)(C$_6$H$_5$)$_3$)$^+$)
Elemental analysis C$_{42}$H$_{41}$BOS
Calculated C: 83.43%, H: 6.83%
Found C: 83.54%, H: 6.91%

EXAMPLE 47

Synthesis of bis(p-tert-butylphenyl)phenacylsulfonium-(sec-butphenylborate

A solution of 2.61 g of lithium sec-butyltriphenylborate in 50 ml of acetonitrile was added to solution of 5.00 g of bis(p-tert-butylphenyl)phenacylsulfonium hexafluorophosphate in 100 ml of acetonitrile and the resultant mixture was stirred at room temperature for 30 minutes. Then, 200 ml of water was added. The resultant precipitate of a yellow oily component was recovered, and 100 ml of dichloromethane was added. The dichloromethane layer was washed with water, dried and concentrated to give 4.32 of bis(p-tert-butylphenyl)phenacylsulfonium-(sec-butyl)triphenylborate.

FD-MS m/z 417 ( (M-B(C$_4$H$_9$) (C$_6$H$_5$)$_3$)$^+$)
Elemental analysis C$_{50}$H$_{57}$BOS
Calculated C: 83.77%, H: 8.01%
Found C: 83.63%, H: 8.13%

EXAMPLE 48

Synthesis of bis(p-tolyl)(p-nitrophenacyl)-sulfonium-n-butyl-tris(p-methoxyphenyl)borate A solution of 4.43 g of tetramethylammonium-tert-butyl-tris(p-methoxyphenyl)borate in 50 ml of acetone was added to a solution of 5.00 g of bis(p-tolyl)(p-nitrophenacyl)sulfonium hexafluorophosphate in 100 ml of acetonitrile, and the resultant mixture was stirred at room temperature for 30 minutes. Then, 200 ml of water was added. The resultant precipitate of yellow oily component was recovered, and 100 ml of dichloromethane was added. The dichloromethane layer was washed with water, dried and concentrated to give 2.27 of bis(p-tolyl)(p-nitrophenacyl)sulfonium-tert-butyl-tris(p-methoxyphenyl)borate.

FD-MS m/z 378 ( (M-B(C$_4$H$_9$) (C$_6$H$_4$OCH$_3$)$_3$)$^+$)
Elemental analysis C$_{47}$H$_{50}$BNO$_6$S
Calculated C: 73.53%, H: 6.56%, N: 1.82%
Found C: 73.42%, H: 6.64, N: 1.78%

EXAMPLE 49

Synthesis of bis(p-chlorophenyl)-(p-methoxyphenacyl)sulfonium-methyl-tris(p-fluorophenyl)borate A solution of 2.80 g of lithium methyl-tris(p-fluorophenyl)borate in 50 ml of acetonitrile was added to a solution of 5.00 g of bis(p-chlorophenyl)(p-methoxyphenacyl)sulfonium hexafluorophosphate in 100 ml of acetonitrile, and the resultant mixture was stirred at room temperature for 30 minutes. Then, 200 ml of methanol was added. The resultant precipitate of a crystal was recovered, and 100 ml of dichloromethane was added. The dichloromethane layer was washed with water, dried and concentrated to give 3.31 of bis(p-chlorophenyl)-(p-methoxyphenacyl)sulfonium-methyl-tris(p-fluorophenyl)borate.

FD-MS m/z 403 ((M-B(CH$_3$)(C$_6$H$_4$F)$_3$)$^+$)
Elemental analysis C$_{40}$}H$_{32}$BCl$_2$F$_3$O$_2$S
Calculated C: 67.15%, H: 4.51%
Found C: 67.09%, H: 4.72%

EXAMPLE 50

Synthesis of phenyl(1-naphthyl)(1-naphthyl-carbonylmethyl)sulfonium-(2-tert-butylethenyl)-tris(p-bromophenyl)borate A solution of 5.58 g of lithium (2-tert-butylethenyl)tris(p-bromophenyl)borate in 50 ml of acetonitrile was added to a solution of 6.41 g of phenyl(1-naphthyl)(1-naphthyl-carbonylmethyl)sulfonium hexafluoroantimonate in 100 ml of acetonitrile, and the resultant mixture was stirred at room temperature for 30 minutes. Then, 200 ml of water was added. The resultant precipitate of a yellow oily component was recovered, and 100 ml of dichloromethane was added. The dichloromethane layer was washed with water, dried and concentrated to give 4.27 of phenyl(1-naphthyl)(1-naphthyl-carbonylmethyl)sulfonium-(2-tert-butylethenyl-)tris(p-bromophenyl)borate.

FD-MS m/z 405 ((M-B(C$_6$H$_{11}$)(C$_6$H$_4$Br)$_3$)$^+$)
Elemental analysis C$_{52}$H$_{44}$BBr$_3$OS
Calculated C: 64.55%, H: 4.58%
Found C: 64.39%, H: 4.69%

EXAMPLE 51

Synthesis of diphenyl-p-fluorophenacylsulfonium-(2-tert-butylethenyl)trimesitylborate A solution of 5.59 g of sodium (2-tert-butylethenyl)trimesitylborate in 50 ml of acetone was added to a solution of 5.00 g of diphenyl-p-fluorophenacylsulfonium perchlorate in 100 ml of acetonitrile, and the resultant mixture was stirred at room temperature for 30 minutes. Then, 200 ml of water was added. The resultant precipitate of a yellow oily component was recovered, and 100 ml of dichloromethane was added. The dichloromethane layer was washed with water, dried and concentrated to give 3.11 of diphenyl-p-fluorophenacylsulfonium-(2-tert-butylethenyl)trimesitylborate.

FD-MS m/z 323 ((M-B$(C_6H_9)(C_6H_2(CH_3)_3)_3)^+$)

Elemental analysis $C_{53}H_{58}BFOS$

Calculated C: 82.36%, H: 7.56%

Found C: 82.19%, H: 7.42%

EXAMPLE 52

Synthesis of phenyl(9-anthryl)(p-chlorophenacyl)-sulfonium-(tert-butyl)triethylborate A solution of 1.29 g of lithium tert-butyltriethylborate in 50 ml of acetonitrile was added to a solution of 5.00 g of phenyl(9-anthryl)(p-chlorophenacyl)sulfonium hexafluoroarsenate in 100 ml of acetonitrile, and the resultant mixture was stirred at room temperature for 30 minutes. Then, 200 ml of water was added. The resultant precipitate of a yellow oily component was recovered, and 100 ml of dichloromethane was added. The dichloromethane layer was washed with water, dried and concentrated to give 2.43 of phenyl(9-anthryl)(p-chlorophenacyl)sulfonium-(tert-butyl)triethylborate.

FD-MS m/z 439 ((M-B(tert-$C_4H_9)(C_2H_5)_3)^+$)

Elemental analysis $C_{38}H_{44}BClOS$

Calculated C: 76.70%, H: 7.45%

Found C: 76.58%, H: 7.29%

EXAMPLE 53

Synthesis of diphenyl(p-bromophenacyl)sulfonium-pbenyltri-n-butylborate

A solution of 2.82 g of lithium phenyltri-n-butylborate in 50 ml of acetonitrile was added to a solution of 5.00 g of diphenyl(p-bromophenacyl)sulfonium tetrafluoroborate in 100 ml of acetonitrile, and the resultant mixture was stirred at room temperature for 30 minutes. Then, 200 ml of water was added. The resultant precipitate of a yellow oily component was recovered, and 100 ml of dichloromethane was added. The dichloromethane layer was washed with water, dried and concentrated to give 2.23 of diphenyl(p-bromophenacyl)sulfonium-phenyltri-n-butylborate.

FD-MS m/z 383 ((M-B$(C_6H_5)(C_4H_9)_3)^+$)

Elemental analysis $C_{38}H_{48}BBrOS$

Calculated C: 70.92%, H: 7.52%

Found C: 71.05%, H: 7.39%

EXAMPLE 54

Synthesis of diphenyl(p-cyanophenacyl)sulfonium-allyltriethylborate

A solution of 1.75 g of lithium allyltriethylborate in 50 ml of acetonitrile was added to solution of 5.00 g of diphenyl(p-cyanophenacyl)sulfonium tetrafluoroborate in 100 ml of acetonitrile, and the resultant mixture was stirred at room temperature for 30 minutes. Then, 200 ml of water was added. The resultant precipitate of a yellow oily component was recovered, and 100 ml of dichloromethane was added. The dichloromethane layer was washed with water, dried and concentrated to give 3.41 g of diphenyl(p-cyanophenacyl)sulfoniumallyltriethylborate.

FD-MS m/z 330 ((M-B$(CH_2CHCH_2)(C_2H_5)_3)^+$)

Elemental analysis $C_{30}H_{36}BNOS$

Calculated C: 76.75%, H: 7.73%, N: 2.98%

Found C: 76.82%, H: 7.82%, N: 2.89%

EXAMPLE 55

Synthesis of diphenyl(p-methylphenacylsulfonium-benzyltriethylborate

A solution of 2.07 g of lithium benzyltriethylborate in 50 ml of acetonitrile was added to solution of 5.00 g of diphenyl(p-methylphenacyl)sulfonium (p-toluenesulfonate) in 100 ml of acetonitrile, and the resultant mixture was stirred at room temperature for 30 minutes. Then, 200 ml of water was added. The resultant precipitate of a yellow oily component was recovered, and 100 ml of dichloromethane was added. The dichloromethane layer was washed with water, dried and concentrated to give 2.12 g of diphenyl(p-methylphenacyl)sulfonium-benzyltriethylborate.

FD-MS m/z 319 ((M-B$(CH_2C_6H_5)(C_2H_5)_3)^+$)

Elemental analysis $C_{34}H_{41}BOS$

Calculated C: 80.30%, H: 8.13%

Found C: 80.27%, H: 8.05%

EXAMPLE 56

Synthesis of diphenylphenacyloxosulfonium-n-butyltriphenylborate

A solution of 5.00 g of lithium n-butyl triphenylborate in 50 ml of tetrahydrofuran was added to a solution of 6.72 g of diphenylphenacyloxosulfonium perchlorate in 100 ml of acetonitrile, and the resultant mixture was stirred at room temperature for 30 minutes. Then, 200 ml of water was added. The resultant precipitate of a yellow oily component was recovered, and 100 ml of dichloromethane was added. The dichloromethane layer was washed with water, dried and concentrated to give 3.87 g of diphenylphenacyloxosulfonium-n-butyltriphenylborate.

FD-MS m/z 321 ((M-B$(C_4H_9)(C_6H_5)_3)^+$)

Elemental analysis $C_{42}H_{41}BO_2S$

Calculated C: 81.28%, H: 6.66%

Found C: 8.32%, H: 6.72%

EXAMPLE 57

Synthesis of bis(p-tert-butylphenyl)phenacyl-oxosulfonium-(sec-butyl)triphenylborate A solution of 2.54 g of lithium sec-butyltriphenylborate in 50 ml of acetonitrile was added to a solution of 5.00 g of bis(p-tert-butylphenyl)phenacyloxosulfonium hexafluorophosphate in 100 ml of acetonitrile, and the resultant mixture was stirred at room temperature for 30 minutes. Then, 200 ml of water was added. The resultant precipitate of a yellow oily component was recovered, and 100 ml of dichloromethane was added. The dichloromethane layer was washed with water, dried and concentrated to give 4.43 g of bis(p-tert-butylphenyl)phenacyloxosulfonium-(sec-butyl)triphenylborate.

FD-MS m/z 435 ((M-B($C_4H_9$) ($C_6H_5$)$_3$)$^+$)

Elemental analysis $C_{50}H_{57}BO_2S$

Calculated C: 81.94%, H: 7.84%

Found C: 82.02%, H: 7.94%

EXAMPLE 58

Synthesis of bis(p-chlorophenyl)(p-methoxyphenacyloxosulfonium-methyl-tris (p-fluorophenyl)-borate A solution of 2.62 g of lithium methyl-tris(p-fluorophenyl)borate in 50 ml of acetonitrile was added to a solution of 5.00 g of bis(p-chlorophenyl)(p-methoxyphenacyl)oxosulfoniumhexafluorophosphate in 100 ml of acetonitrile, and the resultant mixture was stirred at room temperature for 30 minutes. Then, 200 ml of water was added. The resultant precipitate of a yellow oily component was recovered, and 100 ml of dichloromethane was added. The dichloromethane layer was washed with water, dried and concentrated to give 3.26 g of bis(p-chlorophenyl)(p-methoxyphenacyl)oxosulfonium-methyl-tris(p-fluorophenyl)borate.

FD-MS m/z 419 ((M-B($CH_3$)($C_6H_4F$)$_3$)$^+$)

Elemental analysis $C_{40}H_{32}BCl_2F_3O_3S$

Calculated C: 65.68%, H: 4.41%

Found C: 65.78 %, H: 4.52 %

EXAMPLE 59

Synthesis of diphenyl(p-bromophenacyl)-oxosulfonium-phenyltri-n-butylborate

A solution of 2.82 g of lithium phenyltrin-butylborate in 50 ml of acetonitrile was added to a solution of 5.00 g of diphenyl(p-bromophenyl)-oxosulfonium tetrafluoroborate in 100 ml of acetonitrile, and the resultant mixture was stirred at room temperature for 30 minutes. Then, 200 ml of water was added. The resultant precipitate of a yellow oily component was recovered, and 100 ml of dichloromethane was added. The dichloromethane layer was washed with water, dried and concentrated to give 2.23 g of diphenyl (p-bromophenacyl)oxosulfoniumphenyl tri-n-butylborate.

FD-MS m/z 400 ((M-B($C_6H_5$) ($C_4H_9$)$_3$)$^+$)

Elemental analysis $C_{38}H_{48}BBrO_2S$

Calculated C: 70.92%, H: 7.52%

Found C: 71.05%, H: 7.39%

EXAMPLE 60

Synthesis of diphenylbenzylsulfonium-n-butyltriphenylborate

A solution of 4.05 g of lithium n-butyltriphenylborate in 50 ml of acetonitrile was added to a solution of 5.00 g of diphenylbenzylsulfonium tetrafluoroborate in 100 ml of acetonitrile, and the resultant mixture was stirred at room temperature for 30 minutes. Then, 200 ml of water was added. The resultant precipitate of a yellow oily component was recovered, and 100 ml of dichloromethane was added. The dichloromethane layer was washed with water, dried and concentrated to give 2.95 g of diphenylbenzylsulfonium-n-butyltriphenylborate.

FD-MS m/z 277 ( (M-B($C_4H_9$) ($C_6H_5$)$_3$)$^+$)

Elemental analysis $C_{41}H_{41}BS$

Calculated C: 85.40%, H: 7.17%

Found C: 85.32%, H: 7.04%

EXAMPLE 61

Synthesis of diphenyl(p-cyanobenzyl)sulfonium-sec-butyl-triphenylborate

A solution of 3.30 g of lithium sec-butyl triphenylborate in 50 ml of acetonitrile was added to a solution of 5.00 g of diphenyl(p-cyanobenzyl)sulfonium hexafluorophosphatc in 100 ml of acetonitrile, and the resultant mixture was stirred at room temperature for 30 minutes. Then, 200 ml of water was added. The resultant precipitate of a yellow oily component was recovered, and 100 ml of dichloromethane was added. The dichloromethane layer was washed with water, dried and concentrated to give 2.82 g of diphenyl (p-cyanobenzyl)sulfonium-sec-butyl-triphenylborate.

FD-MS m/z 302 ((M-B($C_4H_9$)($C_6H_5$)$_3$)$^+$)

Elemental analysis $C_{42}H_{40}BNS$

Calculated C: 83.85%, H: 6.70%, N: 2.33%

Found C: 83.95%, H: 6.64%, N: 2.28%

EXAMPLE 62

Synthesis of bis(p-tert-butylphenyl)(p-chlorobenzyl)sulfonium-methyltris(p-methoxyphenyl)borate A solution of 3.70 g of tetramethylammonium methyl-tris(p-methoxyphenyl)borate in 50 ml of acetonitrile was added to a solution of 5.00 g of bis(p-tert-butylphenyl)(p-chlorobenzyl)sulfonium hexafluorophosphate in 100 ml of acetonitrile, and the resultant mixture was stirred at room temperature for 30 minutes. Then, 200 ml of methanol was added. The resultant precipitate of a crystal was recovered, and 100 ml of dichloromethane was added. The dichloromethane layer was washed with water, dried and concentrated to give 2.31 g of bis(p-tert-butylphenyl)(p-chlorobenzyl)sulfonium-methyltris(p-methoxyphenyl)borate.

FD-MS m/z 423 ((M-B($CH_3$)(($C_6H_4OCH_3$)$_3$)$^+$)

Elemental analysis $C_{49}H_{56}BClO_3S$

Calculated C: 76.30%, H: 7.32%

Found C: 76.21%, H: 7.18%

EXAMPLE 63

Synthesis of bis(p-chlorophenyl) (p-bromobenzyl)sulfonium-(2-phenylethenyl) tris(p-fluorophenyl)borate A solution of 3.56 g of lithium (2-phenylethenyl)tris(p-fluorophenyl)borate in 50 ml of acetonitrile was added to a solution of 5.00 g of bis(p-chlorophenyl)(p-bromobenzyl)sulfonium hexafluorophosphate in 100 ml of acetonitrile, and the resultant mixture was stirred at room temperature for 30 minutes. Then, 200 ml of water was added. The resultant precipitate of a yellow oily component was recovered, and 100 ml of dichloromethane was added. The dichloromethane layer was washed with water, dried and concentrated to give 1.85 g of bis(p-chlorophenyl)(p-bromobenzyl)sulfonium-(2-phenylethenyl)tris(p-fluorophenyl)borate.

FD-MS m/z 423 ((M-B(CHCHC$_6$H$_5$)(C$_6$H$_4$F)$_3$)$^+$)

Elemental analysis C$_{45}$H$_{33}$BBrCl$_2$F$_3$S

Calculated C: 65.56%, H: 4.04%

Found C: 65.42%, H: 3.99%

EXAMPLE 64

Synthesis of phenyl(1-naphthyl) (1-naphthylmethyl)-sulfonium-allyltris (p-bromophenyl)borate A solution of 4.30 g of lithium allyltris(p-bromophenyl)borate in 50 ml of acetonitrile was added to a solution of 5.00 g of phenyl (1-naphthyl) (1-naphthylmethyl)sulfonium hexafluoroantimonate in 100 ml of acetone, and the resultant mixture was stirred at room temperature for 30 minutes. Then, 200 ml of water was added. The resultant precipitate of a yellow oily component was recovered, and 100 ml of dichloromethane was added. The dichloromethane layer was washed with water, dried and concentrated to give 2.52 g of phenyl(1-naphthyl)(1-naphthylmethyl) sulfonium-allyltris(p-bromophenyl)borate.

FD-MS m/z 377 ( (M-B(CH$_2$CHCH$_2$) (C$_6$H$_4$Br)$_3$)$^+$)

Elemental analysis C$_{48}$H$_{38}$BBr$_3$S

Calculated C: 64.24%, H: 4.27%

Found C: 64.36%, H: 4.22%

EXAMPLE 65

Synthesis of phenyl(p-phenylthiophenyl) (p-nitrobenzyl)sulfonium-benzyltriphenylborate A solution of 3.21 g of lithium benzyl triphenylborate in 50 ml of acetonitrile was added to a solution of 5.00 g of phenyl(p-phenylthiophenyl)(p-nitrobenzyl)sulfonium perchlorate in 100 ml of acetonitrile, and the resultant mixture was stirred at room temperature for 30 minutes. Then, 200 ml of water was added. The resultant precipitate of a yellow oily component was recovered, and 100 ml of dichloromethane was added. The dichloromethane layer was washed with water, dried and concentrated to give 2.42 g of phenyl(p-phenylthiophenyl)-(p-nitrobenzyl)sulfonium-benzyltriphenylborate.

FD-MS m/z 430 ((M-B(CH$_2$C$_6$H$_5$)((C$_6$H$_5$)$_3$)$^+$)

Elemental analysis C$_{50}$H$_{42}$BNO$_2$S$_2$

Calculated C: 78.62%, H: 5.54%, N: 1.83%

Found C: 78.54%, H: 5.41%, N: 1.86%

EXAMPLE 66

Synthesis of diphenyl(p-methylbenzyl)sulfonium-(tert-butyl)triethylborate

A solution of 1.69 g of lithium tert-butyltriethylborate in 50 ml of acetonitrile was added to solution of 5.00 g of diphenyl(p-methylbenzyl)sulfonium hexafluoroarsenate in 100 ml of acetonitrile, and the resultant mixture was stirred at room temperature for 30 minutes. Then, 200 ml of water was added. The resultant precipitate of a yellow oily component was recovered, and 100 ml of dichloromethane was added. The dichloromethane layer was washed with water, dried and concentrated to give 1.28 g of diphenyl(p-methylbenzyl)sulfonium-(tert-butyl)triethylborate.

FD-MS m/z 291 ((M-B(CH$_2$C$_6$H$_4$CH$_3$)((C$_2$H$_5$)$_3$)$^+$)

Elemental analysis C$_{30}$H$_{43}$BS

Calculated C: 80.69%, H: 9.71%

Found C; 80.42%, H: 9.62%

EXAMPLE 67

Synthesis of diphenyl(p-methoxybenzyl)sulfonium-phenyltri-n-butylborate

A solution of 3.26 g of lithium phenyltrin-butylborate in 50 ml of acetonitrile was added to a solution of 5.00 g of diphenyl(p-methoxybenzyl)sulfonium tetrafluoroarsenate in 100 ml of acetonitrile, and the resultant mixture was stirred at room temperature for 30 minutes. Then, 200 ml of water was added. The resultant precipitate of a yellow oily component was recovered, and 100 ml of dichloromethane was added. The dichloromethane layer was washed with water, dried and concentrated to give 1.99 g of diphenyl(p-methoxybenzyl)sulfonium-phenyltri-n-butylborate.

FD-MS m/z 307 ((M-B(C$_6$H$_5$)((C$_4$H$_9$)$_3$)$^+$)

Elemental analysis C$_{38}$H$_{51}$BOS

Calculated C: 80.54%, H: 9.07%

Found C: 80.53%, H: 9.12%

EXAMPLE 68

Synthesis of diphenyl(p-phenylthiobenzyl)-sulfonium-benzyltriethylborate

A solution of 1.85 g of lithium benzyltriethylborate in 50 ml of acetonitrile was added to a solution of 5.00 g of diphenyl(p-phenylthiobenzyl)sulfonium hexafluorophosphate in 100 ml of acetonitrile, and the resultant mixture was stirred at room temperature for 30 minutes. Then, 200 ml of water was added. The resultant precipitate of a yellow oily component was recovered, and 100 ml of dichloromethane was added. The dichloromethane layer was washed with water, dried and concentrated to give 2.04 g of diphenyl(p-phenylthiobenzyl)sulfonium-benzyltriethylborate.

FD-MS m/z 385 ((M-B(CH$_2$C$_6$H$_5$)((C$_2$H$_5$)$_3$)$^+$)

Elemental analysis C$_{38}$H$_{43}$BS$_2$

Calculated C: 79.42%, H: 7.54%

Found C: 79.31%, H: 7.39%

EXAMPLE 69

Synthesis of diphenybenzyloxosulfonium-n-butyltriphenylborate

A solution of 4.00 g of lithium n-butyltriphenylborate in 50 ml of tetrahydrofuran was added to a solution of 5.00 g of diphenylbenzyloxosulfonium tetrafluoroborate in 100 ml of acetonitrile, and the resultant mixture was stirred at room temperature for 30 minutes. Then, 200 ml of water was added. The resultant precipitate of a yellow oily component was recovered, and 100 ml of dichloromethane was added. The dichloromethane layer was washed with water, dried and concentrated to give 2.78 g of diphenylbenzyloxosulfonium-n-butyl triphenylborate.

FD-MS m/z 293 ((M-B(C$_{41}$H$_9$)(C$_6$H$_5$)$_3$)$^+$)

Elemental analysis C$_{41}$H$_{41}$BOS

Calculated C: 83.09%, H: 6.97%

Found C: 83.15%, H: 7.01%

EXAMPLE 70

Synthesis of diphenyl(p-cyanobenzyl)oxosulfonium-(sec-butyl)triphenylborate

A solution of 3.25 g of lithium sec-butyltriphenylborate in 50 ml of dioxane was added to a solution of 5.00 g of diphenyl(p-cyanobenzyl)oxosulfonium hexafluoroborate in 100 ml of dioxane, and the resultant mixture was stirred at room temperature for 30 minutes. Then, 200 ml of methanol was added. The resultant precipitate of a crystal was recovered, and 100 ml of dichloromethane was added. The dichloromethane layer was washed with water, dried and concentrated to give 2.41 g of diphenyl(p-cyanobenzyl)oxosulfonium-(sec-butyl)triphenylborate.

FD-MS m/z 318 $((M-B(C_4H_9)(C_6H_5)_3)^+)$

Elemental analysis $C_{42}H_{40}BNOS$

Calculated C: 81.67%, H: 6.53%, N: 2.27%

Found C: 81.49%, H: 6.47%, N: 2.29%

EXAMPLE 71

Synthesis of bis(p-chlorophenyl)(p-bromobenzyl)oxosulfonium-(2-phenylethenyl)tris(p-fluorophenyl)borate A solution of 3.48 g of lithium (2-phenylethenyl)tris(p-fluorophenyl)borate in 50 ml of acetonitrile was added to a solution of 5.00 g of bis(p-chlorophenyl)(p-bromobenzyl)oxosulfonium hexafluorophosphatc in 100 ml of acetonitrile, and the resultant mixture was stirred at room temperature for 30 minutes. Then, 200 ml of water was added. The resultant precipitate of a yellow oily component was recovered, and 100 ml of dichloromethane was added. The dichloromethane layer was washed with water, dried and concentrated to give 1.95 g of (p-chlorophenyl)(p-bromobenzyl)oxosulfonium(2-phenylethenyl)tris(p-fluorophenyl)borate.

FD-MS m/z 439 $((M-B(CHCHC_6H_5)(C_6H_4F)_3)^+)$

Elemental analysis $C_{45}H_{33}BBrCl_2F_3OS$

Calculated C: 64.31%, H: 3.96%

Found C: 64.12%, H: 3.92%

EXAMPLE 72

Synthesis of diphenyl(p-methoxybenzyl)oxosulfonium-phenyltri-n-butylborate

A solution of 3.14 g of lithium phenyltri-n-butylborate in 50 ml of acetonitrile was added to a solution of 5.00 g of diphenyl(p-methoxybenzyl)oxosulfonium tetrafluoroborate in 100 ml of acetonitrile, and the resultant mixture was stirred at room temperature for 30 minutes. Then, 200 ml of water was added. The resultant precipitate of a yellow oily component was recovered, and 100 ml of dichloromethane was added. The dichloromethane layer was washed with water, dried and concentrated to give 2.25 g of diphenyl(p-methoxybenzyl)oxosulfonium-phenyltri-n-butylborate.

FD-MS m/z 323 $((M-B(C_6H_5)((C_4H_9)_3)^+)$

Elemental analysis $C_{38}H_{51}BO_2S$

Calculated C: 78.33%, H: 8.82%

Found C: 78.12%, H: 8.92%

EXAMPLE 73

Synthesis of diphenylallylsulfonium-n-butyltriphenylborate

A solution of 4.70 g of lithium n-butyltriphenylborate in 50 ml of acetonitrile was added to a solution of 5.00 g of diphenylallylsulfonium tetrafluoroborate in 100 ml of acetonitrile, and the resultant mixture was stirred at room temperature for 30 minutes. Then, 200 ml of water was added. The resultant precipitate of a yellow oily component was recovered, and 100 ml of dichloromethane was added. The dichloromethane layer was washed with water, dried and concentrated to give 3.87 g of diphenylallylsulfonium-n-butyltriphenylborate.

FD-MS m/z 227 $((M-B(C_4H_9)((C_6H_5)_3)^+)$

Elemental analysis $C_{37}H_{39}BS$

Calculated C: 84.39%, H: 7.47%

Found C: 84.42%, H: 7.34%

EXAMPLE 74

Synthesis of diphenyl(3,3-dicyano-2-phenyl-2-propenyl)sulfonium-(sec-butyl)triphenylborate A solution of 3.35 g of lithium sec-butyltriphenylborate in 50 ml of acetonitrile was added to a solution of 5.00 g of diphenyl(3,3-dicyano-2-phenyl-2-propenyl)sulfonium tetrafluoroborate in 100 ml of acetonitrile, and the resultant mixture was stirred at room temperature for 30 minutes. Then, 200 ml of water was added. The resultant precipitate of a yellow oily component was recovered, and 100 ml of dichloromethane was added. The dichloromethane layer was washed with water, dried and concentrated to give 2.87 g of diphenyl(3,3-dicyano-2-phenyl-2-propenyl)sulfonium-(sec-butyl)triphenylborate.

FD-MS m/z 353 $((M-B(C_4H_9)((C_6H_5)_3)^+)$

Elemental analysis $C_{45}H_{41}BN_2S$

Calculated C: 82.81%, H: 6.33%, N: 4.29%

Found C: 82.72%, H: 6.27%, N: 4.34%

EXAMPLE 75

Synthesis of bis(p-chlorophenyl)(3,3-dicyano-2-methyl-2-propenyl)sulfonium-methyltris(p-methoxyphenyl)borate A solution of 4.17 g of lithium tetramethylammonium methyltris(p-methoxyphenyl)borate in 50 ml of acetonitrile was added to a solution of 5.00 g of bis(p-chlorophenyl)(3,3-dicyano-2-methyl-2-propenyl)sulfonium hexafluorophosphate in 100 ml of acetonitrile, and the resultant mixture was stirred at room temperature for 30 minutes. Then, 200 ml of water was added. The resultant precipitate of a yellow oily component was recovered, and 100 ml of dichloromethane was added. The dichloromethane layer was washed with water, dried and concentrated to give 2.85 g of bis(p-chlorophenyl)(3,3-dicyano-2-methyl-2-propenyl) sulfonium-methyltris(p-methoxyphenyl)borate.

FD-MS m/z 359 $((M-B(CH_3)((C_6H_4OCH_3)_3)^+)$

Elemental analysis $C_{40}H_{37}BCl_2N_2O_3S$

Calculated C: 67.90%, H: 5.27%, N: 3.96%

Found C: 68.02%, H: 5.34%, N: 4.02%

EXAMPLE 76

Synthesis of bis(p-tert-butylphenyl)[3,3-bis-(methoxycarbonyl)-2-phenyl-2-propenyl] sulfonium-vinyltris(p-fluorophenyl)borate A solution of 4.17 g of lithium vinyltris(p-fluorophenyl)borate in 50 ml of acetonitrile was added to solution of 5.00 g of bis(p-tert-butylphenyl)[3,3-bis(methoxycarbonyl)-2-phenyl-2-propenyl]sulfonium perchlorate in 100 ml of acetonitrile, and the resultant mixture was stirred at room temperature for 30 minutes. Then, 200 ml of water was added. The resultant precipitate of a yellow oily component was recovered, and 100 ml of dichloromethane was added. The dichloromethane layer was washed with water, dried and concentrated to give 2.85 g of bis(p-tert-butylphenyl)[3,3-bis(methoxycarbonyl)-2-phenyl-2-propenyl]sulfonium-vinyltris(p-fluorophenyl)borate.

FD-MS m/z 531 $((M-B(CHCH_2)(C_6H_4F)_3)^+)$

Elemental analysis $C_{53}H_{54}BF_3O_4S$

Calculated C: 74.47%, H: 6.37%

Found C: 74.56%, H: 6.29%

EXAMPLE 77

Synthesis of bis(p-fluorophenyl)(3,3-dicyano-2-p-tolyl-2-propenyl)sulfonium-phenyltri-n-butyl-borate A solution of 2.38 g of lithium phenyltri-n-butylborate in 50 ml of acetonitrile was added to a solution of 5.00 g of bis(p-fluorophenyl)(3,3-dicyano-2-p-tolyl-2-propenyl)sulfonium (p-toluenesulfonate) in 100 ml of acetonitrile, and the resultant mixture was stirred at room temperature for 30 minutes. Then, 200 ml of water was added. The resultant precipitate of a yellow oily component was recovered, and 100 ml of dichloromethane was added. The dichloromethane layer was washed with water, dried and concentrated to give 2.09 g of bis(p-fluorophenyl) (3,3-dicyano-2-p-tolyl-2-propenyl)sulfonium-phenyltri-n-butylborate.

FD-MS m/z 403 $((M-B(C_6H_5)(C_4H_9)_3)^+)$

Elemental analysis $C_{42}H_{46}BF_2N_2S$

Calculated C: 76.12%, H: 7.45%, N: 4.23%

Found C: 76.23%, H: 7.39%, N: 4.32%

EXAMPLE 78

Synthesis of phenyl(1-naphthyl)[3,3-dicyano-2-(p-chlorophenyl)-2-propenyl] sulfonium-allyltriethylborate A solution of 1.16 g of lithium allyltriethylborate in 50 ml of acetonitrile was added to a solution of 5.00 g of phenyl(1-naphthyl)[3,3-dicyano-(2-chlorophenyl)-2-propenyl] sulfonium hexafluoroarserate in 100 ml of acetonitrile, and the resultant mixture was stirred at room temperature for 30 minutes. Then, 200 ml of water was added. The resultant precipitate of a yellow oily component was recovered, and 100 ml of dichloromethane was added. The dichloromethane layer was washed with water, dried and concentrated to give 1.53 g of phenyl(1-naphthyl)[ 3,3-dicyano-2-(p-chlorophenyl)-2-propenyl]sulfoniumallyltricthylborate.

FD-MS m/z 437 $((M-B(CH_2CHCH_2)(C_2H_5)_3)^+)$

Elemental analysis $C_{36}H_{38}BClN_2S$

Calculated C: 74.93%, H: 6.64%, N: 4.86%

Found C: 75.02%, H: 6.54%, N: 4.92%

EXAMPLE 79

Synthesis of diphenylallyloxosulfonium-n-butyltriphenylborate

A solution of 4.70 g of lithium n-butyltriphenylborate in 50 ml of acetonitrile was added to a solution of 5.00 g of diphenylallyloxosulfonium tetrafluoroborate in 100 ml of acetonitrile, and the resultant mixture was stirred at room temperature for 30 minutes. Then, 200 ml of water was added. The resultant precipitate of a yellow oily component was recovered, and 100 ml of dichloromethane was added. The dichloromethane layer was washed with water, dried and concentrated to give 3.87 g of diphenylallyloxosulfonium-n-butyltriphenylborate.

FD-MS m/z 243 $((M-B(n-C_4H_9)(C_6H_5)_3)^+)$

Elemental analysis $C_{37}H_{39}BOS$

Calculated C: 81.91%, H: 7.25%

Found C: 82.01%, H: 7.32%

EXAMPLE 80

Synthesis of diphenyl(3,3-dicyano-2-phenyl-2-propenyl)oxosulfonium-(sec-butyl)triphenyl-borate A solution of 3.35 g of lithium sec-butyltriphenylborate in 50 ml of acetonitrile was added to a solution of 5.00 g of diphenyl(3,3-dicyano-2-phenyl-2-propenyl)oxosulfonium tetrafluoroborate in 100 ml of acetonitrile, and the resultant mixture was stirred at room temperature for 30 minutes. Then, 200 ml of water was added. The resultant precipitate of a yellow oily component was recovered, and 100 ml of dichloromethane was added. The dichloromethane layer was washed with water, dried and concentrated to give 2.87 g of diphenyl(3,3-dicyano-2-phenyl-2-propenyl) oxosulfonium-(sec-butyl)triphenylborate.

FD-MS m/z 369 $((M-B(C_4H_9)(C_6H_5)_3)^+)$

Elemental analysis $C_{45}H_{41}BN_2OS$

Calculated C: 80.83%, H: 6.18%, N: 4.19%

Found C: 80.75%, H: 6.24%, N: 4.25%

EXAMPLE 81

Synthesis of bis(p-tert-butylphenyl)[3,3,-bis-methoxycarbonyl)-2-phenyl-2-propenyl]-oxosulfonium-vinyltris(p-fluorophenyl)borate A solution of 4.17 g of lithium vinyltris(p-fluorophenyl)borate in 50 ml of acetonitrile was added to a solution of 5.00 g of bis(p-tert-butylphenyl)[ 3,3-bis(methoxycarbonyl)-2-phenyl-2-propenyl]oxosulfonium perchlorate in 100 ml of acetonitrile, and the resultant mixture was stirred at room temperature for 30 minutes. Then, 200 ml of water was added. The resultant precipitate of a yellow oily component was recovered, and 100 ml of dichloromethane was added. The dichloromethane layer was washed with water, dried and concentrated to give 2.85 g of bis(p-tert-butylphenyl)[3,3-bis(methoxycarbonyl)-2-phenyl-2-propenyl] oxosulfonium-vinyltris(p-fluorophenyl)borate.

FD-MS m/z 547 $((M-B(CHCH_2)(C_6H_4F)_3)^+)$

Elemental analysis $C_{53}H_{54}BF_3O_5S$

Calculated C: 73.10%, H: 6.25%

Found C: 73.21%, H: 6.29%

EXAMPLE 82

Synthesis of bis(p-fluorophenyl)[3,3-dicyano-2-p-tolyl-2-propenyl]sulfonium-phenyltri-n-butylborate A solution of 2.38 g of lithium phenyltri-n-butylborate in 50 ml of acetonitrile was added to a solution of 5.00 g of bis(p-fluorophenyl)[ 3,3-dicyano-2-p-tolyl-2-propenyl]sulfonium (p-toluenesulfonate) in 100 ml of acetonitrile, and the resultant mixture was stirred at room temperature for 30 minutes. Then, 200 ml of water was added. The resultant precipitate of a yellow oily component was recovered, and 100 ml of dichloromethane was added. The dichloromethane layer was washed with water, dried and concentrated to give 2.09 g of bis(p-fluorophenyl)[ 3,3- dicyano-2-p-tolyl-2-pro-penyl]sulfonium-phenyltri-n-butylborate.

FD-MS m/z 419 ((M-B($C_6H_5$)($C_4H_9$)$_3$)$^+$)

Elemental analysis $C_{42}H_{46}BF_2N_2OS$

Calculated C: 74.32%, H: 7.28%, N: 4.13%

Found C: 74.25%, H: 7.34%, N: 4.22%

EXAMPLES 82–117 AND COMPARATIVE EXAMPLES 1–3

50 Parts of pentaerythritol triacrylate as a radical-polymerizable, ethylenically unsaturated compound and 1 part of dimethylphenacylsulfonium-butyltriphenylborate as a polymerization initiator were dissolved in 100 parts of dioxane as a diluent. The resultant mixture was coated on a glass plate to form a coating having a thickness of about 5 microns, and the coating was dried in a hot-air oven at 70° C. for 2 minutes. Further, a polyethylene terephthalate film having a thickness of about 25 microns was tightly attached to the coating to prepare a sample. When the sample was kept in an oven at 150° C. for 10 minutes, the sample was clearly cured to give a polymer product.

Samples were prepared in the same manner as above except that the dimethylphenacylsulfonium-butyltriphenylborate as a polymerization initiator was replaced with dimethylphenacyloxosulfonium-butyltriphenylborate, dimethylbenzylsulfonium-butyltriphenylborate, dimethylbenzyloxosulfonium-butyltriphenylborate, dimethyl-p-chlorophenacylsulfonium-butyltriphenylborate, dimethyl-p-chlorobenzylsulfonium-butyltriphenylborate, dimethyl-p-cyanobenzylsulfonium-butyltriphenylborate, di-tert-butylphenacylsulfonium-butyltriphenylborate, dimethylphcnacylsulfonium-butyltri(methoxyphenyl)borate, dimethylphenacylsulfonium-butyltri(p-fluorophenyl)borate, dimethylphenacylsulfonium-vinyltriphenylborate, dimethylphenacylsulfonium-benzyltriphenylborate, dimethylphenacylsulfonium-tertbutyltriethylborate, dimethylphenacylsulfonium-phenyltriethylborate, tetramethylenephenacylsulfonium-butyltriphenylborate, dimethylallylsulfonium-butyltriphenylborate, dimethylcyanomethylsulfonium-butyltriphenylborate, dimethylethoxycarbonylmethyl-sulfonium-butyltriphenylborate, dimethylvinylsulfonium-butyltriphenylborate, dimethylphenoxyoxosulfonium-butyltriphenylborate, diethylethylthiosulfonium-butyltriphenylborate, dimethyl-N-phenylaminosulfonium-butyltriphenylborate, p-acetoxyphenylbenzylmethylsulfonium-butyltriphenylborate, phenylmethyl(2-phenyl-3,3-dicyanopropen-2-yl)sulfonium-butyltriphenylborate, diphenylbenzylsulfonium-n-butyltriphenylborate, diphenyl(p-cyanobenzyl)sulfonium-n-butyltriphenylborate, diphenyl(p-cyanobenzyl)sulfonium-sec-butyltriphenylborate, diphenylphenacylsulfonium-n-butyltriphenylborate, diphenyl(p-cyanophenacyl)sulfonium-n-butyltriphenylborate, bis(p-chlorophenyl)(p-bromophenacyl)sulfonium-benzyltriphenylborate, diphenylallylsulfonium-n-butyltriphenylborate, diphenyl(2-phenyl-3,3-dicyano-2-propenyl)sulfonium-n-butyltriphenylborate, diphenylcyanomethylsulfonium-n-butyltriphenylborate, diphenylmethoxycarbonylmethylsulfonium-n-butyltriphenylborate, diphenylbenzyloxosulfonium-n-butyltriphenylborate and diphenylphenacyloxosulfonium-n-butyltriphenylborate. When the so-prepared samples were respectively treated in the same manner as above, the samples were cured to give polymer products.

For comparison, samples were prepared in the same manner as above except that the dimethylphenacylsulfonium-butyltriphenylborate as a polymerization initiator was replaced with dimethylphenacylsulfonium-tetrafluoroborate, dimethylphenacylsulfonium-tetraphenylborate, dimethylphenacyloxosulfonium-hexafluorophosphate and dimethylbenzylsulfonium-tetrafluoroborate. When the so-prepared samples were treated in the same manner as above, no polymer products were formed.

EXAMPLES 118–153 AND COMPARATIVE EXAMPLES 4–6

50 Parts of pentaerythritol triacrylate as a radical-polymerizable, ethylenically unsaturated compound and 1 part of dimethylphenacylsulfonium-butyltriphenylborate as a polymerization initiator were dissolved in 100 parts of dioxane as a diluent, The resultant mixture was coated on a glass plate to form a coating having a thickness of about 5 microns. The coating was dried in a hot-air oven at 70° C. for 2 minutes. Then, a polyethylene terephthalate film having a thickness of about 25 μm was tightly attached to the above coating to prepare a sample. When the sample was exposed to a 500 mW high-pressure mercury lamp for 30 seconds, the samples were clearly cured to give a polymer product.

Samples were prepared in the same manner as above except that the dimethylphenacylsulfonium-butyltriphenylborate as a polymerization initiator was replaced with dimethylphenacyloxosulfonium-butyltriphenylborate, dimethylbenzylsulfonium-butyltriphenylborate, dimethylbenzyloxosulfonium-butyltriphenylborate, dimethyl-p-chlorophenacylsulfonium-butyltriphenylborate, dimethyl-p-chlorobenzylsulfonium-butyltriphenylborate, dimethyl-p-cyanobenzylsulfonium-butyltriphenylborate, di-tert-butylphenacylsulfonium-butyltriphenylborate, dimethylphenacylsulfonium-butyltri(methoxyphenyl)borate, dimethylphenacylsulfonium-butyltri(p-fluorophenyl)borate, dimethylphenacylsulfoniumvinyltriphenylborate, dimethylphcnacylsulfonium-benzyltriphenylborate, dimethylphenacylsulfonium-tertbutyltriethylborate, dimethylphenacylsulfoniumphenyltriethylborate, tetramethylenephenacylsulfonium-butyltriphenylborate, dimethylallylsulfonium-butyltriphenylborate, dimethylcyanomethylsulfonium-butyltriphenylborate, dimethylethoxycarbonylmethyl-sulfonium-butyltriphenylborate, dimethylvinylsulfonium-butyltriphenylborate, dimethylphenoxyoxosulfonium-butyltriphenylborate, diethylethylthiosulfonium-butyltriphenylborate, dimethyl-N-phenylaminosulfonium-butyltriphenylborate, p-acetoxyphenylbenzylmethylsulfonium-butyltriphenylborate, phenylmethyl(2-phenyl-3,3-dicyanopropen-2-yl)sulfonium-butyltriphenylborate, diphenylbenzylsulfonium-n-butyltriphenylborate, diphenyl(p-cyanobenzyl)sulfonium-n-butyltriphenylborate, diphenyl(p-cyanobenzyl)sulfonium-sec-butyltriphenylborate, diphenylphenacylsulfonium-n-butyltriphenylborate, diphenyl(p-cyanophenacyl)sulfonium-n-butyltriphenylborate, bis(p-chlorophenyl)(p-bromophenacyl)sulfonium-benzyltriphenylborate, diphenylallylsulfonium-n-butyltriphenylborate, diphenyl(2-phenyl-3,3-dicyano-2-propenyl)sulfonium-n-butyltriphenylborate, diphenylcyanomethylsulfonium-n-butyltriphenylborate, diphenylmethoxycarbonylmethylsulfonium-n-butyltriphenylborate, diphenylbenzyloxosulfonium-n-butyltriphenylborate and diphenylphenacyloxosulfonium-n-butyltriphenylborate. When the so-prepared samples were respectively treated in the same manner as above, the samples were cured to give polymer products.

For comparison, samples were prepared in the same manner as above except that the dimethylphenacylsulfonium-butyltriphenylborate as a polymerization initiator was replaced with dimethylphenacylsulfonium-tetrafluoroborate, dimethylphenacyloxosulfonium-hexafluorophosphate and dimethylbenzylsulfonium-tetrafluoroborate. When the so-prepared samples were treated in the same manner as above, no polymer products were formed.

EXAMPLES 154–184 AND COMPARATIVE EXAMPLES 7–9

A photosensitive liquid was prepared by adding $1.2 \times 10^{-5}$ mol of one of sulfonium or oxosulfonium complex shown in Table 1 as a polymerization initiator to 2 g of a solution containing 360 parts of methyl ethyl ketone as a solvent, 20 parts of polymethyl methacrylate as a binder, 20 parts of pentaerythritol triacrylate as a radical-polymerizable, ethylenically unsaturated compound and 1 part of 3,3'-carbonyl-bis(7-diethylaminocumarin) of the formula (4) as a sensitizer. The above photosensitive liquid was applied to a glass plate with a spin coater to form a coating having a thickness of about 2 μm, and then a 10% polyvinyl alcohol aqueous solution was applied thereto to form a coating having a thickness of about 5 μm as an oxygen barrier layer, whereby a photosensitive plate was obtained. The photosensitive plate was exposed to argon ion laser light (488 nm) having a beam diameter of 1.5 mm for various periods of time and developed with water and toluene. Light energy which gave a cured spot having the same size as the diameter of the laser beam was regarded as sensitivity, and Table 1 shows the light energy as sensitivity.

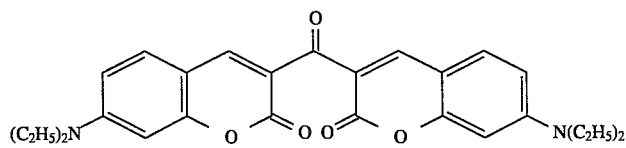

(4)

For comparison, the above procedures were repeated except that the polymerization initiator was replaced with dimethylphenacylsulfonium-tetrafluoroborate, dimethylphenacyloxosulfonium-tetrafluoroborate and tetrabutylammonium-butyltriphenylborate. Table also shows the results on sensitivity.

Table 1 clearly shows that the sulfonium or oxosulfonium complex of the formula (1) as a polymerization initiator gives improved sensitivity over known polymerization initiators such as dimethylphenacylsulfonium-tetrafluoroborate, dimethylphenacyloxosulfonium-tetrafluoroborate and tetrabutylammonium-butyltriphenylborate.

TABLE 1

| Example | Polymerization initiator | Sensitivity (mJ/cm$^2$) |
|---|---|---|
| Ex. 154 | dimethylphenacylsulfonium-butyltriphenylborate | 0.2 |
| Ex. 155 | dimethylphenacylsulfonium-sec-butyltriphenylborate | 0.1 |
| Ex. 156 | dimethylphenacylsulfonium-tert-butyltriphenylborate | 0.1 |
| Ex. 157 | dimethylbenzylsulfonium-butyltriphenylborate | 0.5 |
| Ex. 158 | dimethylbenzylsulfonium-tert-butyltriethylborate | 0.8 |
| Ex. 159 | didodecylbenzylsulfonium-butyltriphenylborate | 0.5 |
| Ex. 160 | dimethyl-p-cyanobenzylsulfonium-butyltriphenylborate | 0.4 |
| Ex. 161 | dimethylphenacylsulfonium-butyltri(p-mehxoyphenyl)borate | 0.2 |
| Ex. 162 | dimethylphenacylsulfonium-butyltri(p-fluorophenyl)borate | 0.2 |
| Ex. 163 | dimethylphenacylsulfonium-sec-butyltri(p-fluorophenyl)borate | 0.1 |
| Ex. 164 | dimethylphenacylsulfonium-tert-butyltri(p-fluorophenyl)borate | 0.1 |
| Ex. 165 | dimethylphenacylsulfonium-butyltri(p-clorophenyl)borate | 0.2 |
| Ex. 166 | dimethylphenacylsulfonium-butyltri(p-bromophenyl)borate | 0.2 |
| Ex. 167 | dimethylphenacylsulfonium-see-butyltri(p-methoxyphenyl)borate | 0.1 |
| Ex. 168 | dimethyl-p-chlorophenacylsulfonium-butyltriphenylborate | 0.2 |
| Ex. 169 | dimethylphenacylsulfonium-tert-butyltriethylborate | 0.8 |
| Ex. 170 | didodecylphenacylsulfonium-butyltriphenylborate | 0.2 |
| Ex. 171 | dimethylbenzyloxosulfonium-butyltriphenylborate | 0.2 |
| Ex. 172 | dimethylphenacyloxosulfonium-butyltriphenylborate | 0.1 |
| Ex. 173 | diphenylbenzylsulfonium-n-butyltriphenylborate | 0.3 |
| Ex. 174 | diphenyl(p-cyanobenzyl)sulfonium-n-butyltriphenylborate | 0.3 |
| Ex. 175 | diphenyl(p-cyanobenzyl)sulfonium-sec-butyltriphenylborate | 0.5 |
| Ex. 176 | diphenylphenacylsulfonium-n-butyltriphenylborate | 0.1 |
| Ex. 177 | diphenyl(p-cyanophenacyl)sulfonium-n-butyltriphenylborate | 0.1 |
| Ex. 178 | bis(p-chlorophenyl)(p-bromophenacyl)sulfonium benzyltriphenylborate | 0.1 |
| Ex. 179 | diphenylallylsulfonium-n-butyltriphenylborate | 0.2 |
| Ex. 180 | diphenyl(2-phenyl-3,3-dicyano-2-propenyl)sulfonium-n-butyltriphenylborate | 0.2 |
| Ex. 181 | diphenylcyanomethylsulfonium-n-butyltriphenylborate | 0.4 |
| Ex. 182 | diphenylmethoxycarbonylmethylsulfonium-n-butyltriphenylborate | 0.4 |

TABLE 1-continued

| Example | Polymerization initiator | Sensitivity (mJ/cm$^2$) |
| --- | --- | --- |
| Ex. 183 | diphenylbenzyloxosulfonium-n-butyltriphenylborate | 0.2 |
| Ex. 184 | diphenylphenacyloxosulfonium-n-butyltriphenylborate | 0.1 |
| CEx. 7 | dimethylphenacylsulfonium-tetrafluoroborate | 4.1 |
| CEx. 8 | dimethylphenacyloxosulfonium-tetrafluoroborate | 3.0 |
| CEx. 9 | tetrabutylammonium-butyltriphenylborate | 1.5 |

Ex. = Example, CEx. = Comparative Example

EXAMPLES 185-186

A photosensitive liquid was prepared by adding $1.2 \times 10^{-5}$ mol of dimethylphenacylsulfonium-butyltriphenylborate to 2 g of a solution containing 360 parts of methyl ethyl ketone as a solvent, 20 parts of polymethyl methacrylate as a binder, 20 parts of pentaerythritol triacrylate as a radical-polymerizable, ethylenically unsaturated compound and 1 part of a sensitizer of the following formula (5) or (6). Then, the above photosensitive liquid was applied to a glass plate with a spin coater to form a coating having a thickness of about 2 μm, and then a 10% polyvinyl alcohol aqueous solution was applied thereto to form a coating having a thickness of about 5 μm as an oxygen barrier layer, whereby a photosensitive plate was obtained. The photosensitive plate was exposed to argon ion laser light (514 nm) having a beam diameter of 1.5 mm or helium neon laser light (633 nm) having a beam diameter of 1.5 mm for various periods of time and developed with water and toluene. Light energy which gave a cured spot having the same size as the width of the laser beam was regarded as sensitivity, and Table 2 shows the light energy as sensitivity.

TABLE 2

| Example | Sensitizer | Wavelength of light (nm) | Sensitivity (mJ/cm$^2$) |
| --- | --- | --- | --- |
| 144 | Formula (4) | 514 | 0.8 |
| 145 | Formula (5) | 633 | 0.4 |

Referential Example

Figure 2:
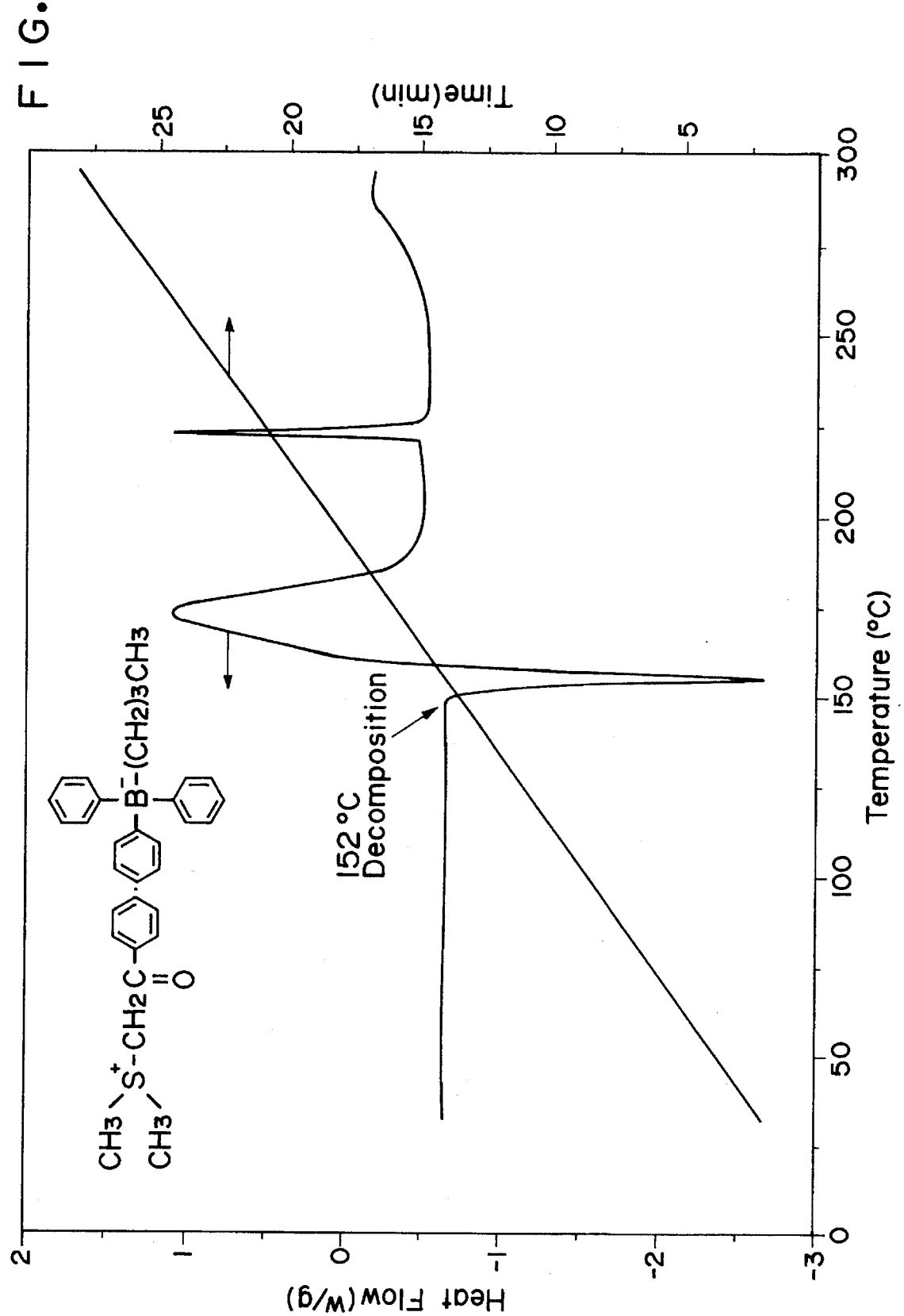
FIG. 2 shows the DSC curve of a sulfonium complex of the present invention, dimethylphenacylsulfonium-butyltriphenyl borate as a polymerization initiator.
Figure 3:
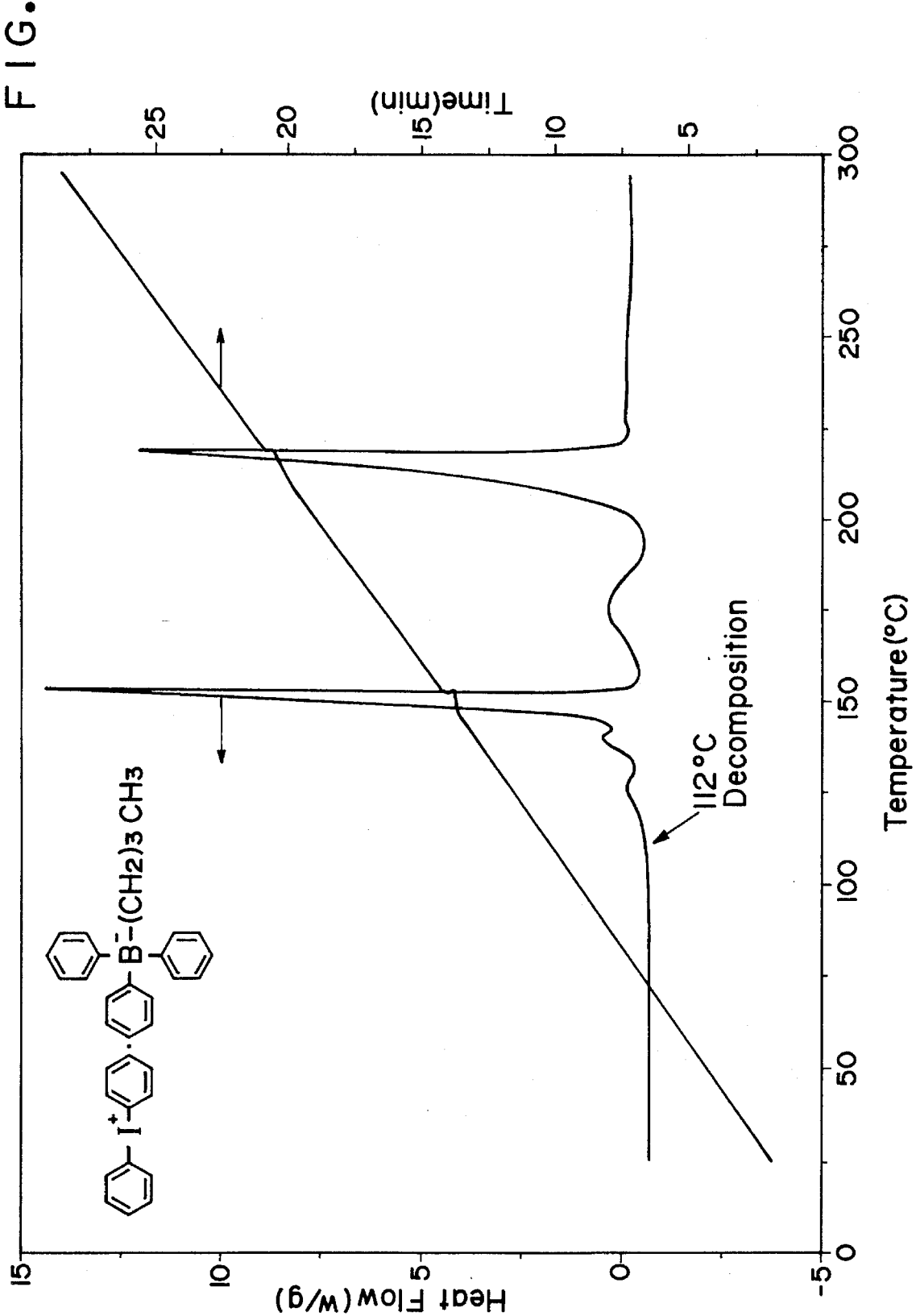
FIG. 3 shows the DSC curve of a diphenyliodonium-butyltriphenyl borate known as a polymerization initiator.

For evaluating thermal stability, dimethylphenacylsulfonium-butyltriphenylborate as a polymerization initiator in the present invention was subjected to differential scanning calorimetry (DSC) at a temperature elevation rate of 10° C./minute from room temperature to about 300° C. FIG. 1 shows the results. Further, diphenyl iodonium-butyl triphenylborate as a known polymerization initiator was subjected to DSC under the same conditions as above, and FIG. 2 shows the results. Dimethylphenacylsulfonium-butyl triphenylborate showed that the temperature at which the DSC curve changed as it decomposed was 152° C. (FIG. 1), while diphenyliodoniumbutyltriphenylborate showed that the corresponding temperature was as low as 112° C. (FIG. 2). It can be therefore understood that the former, dimethylphenacylsulfonium-butyl triphenylborate as a polymerization initiator in the present invention, is thermally more stable than the latter.

What is claimed is:

1. A sulfonium complex or oxosulfonium complex of the formula (1), $$R^4 = S^+ - R^3 . R^5 - B^- - R^7 \quad (1)$$
$$\begin{array}{cc} R^2 & R^6 \\ | & | \\ R^1 & R^8 \end{array}$$

wherein $R^1$ is a benzyl group, a substituted benzyl group, a phenacyl group, a substituted phenacyl group, an aryloxy group, a substituted aryloxy group, an alkenyl group or a substituted alkenyl group, each of $R^2$ and $R^3$ is independently any one of groups defined as $R^1$ an alkyl group, a substituted alkyl group, an aryl group, a substituted aryl group, an aralkyl group, a substituted aralkyl group, an alkynyl group, a substituted alkynyl group, an alicyclic group, a substituted alicyclic group, an alkoxyl group, a substituted alkoxyl group, an alkylthio group, a substituted alkylthio group, an amino group or a substituted amino group, or $R^2$ and $R^3$ may bond together forming a ring structure, $R^4$ is an oxygen atom or lone pair, and each of $R^5$, $R^6$, $R^7$ and $R^8$ is independently an alkyl group, a substituted alkyl group, an aryl group, a substituted aryl group, an aralkyl group, a substituted aralkyl group, an alkenyl group or a substituted alkenyl group, provided that not all of $R^5$, $R^6$, $R^7$ and $R^8$ are aryl groups or substituted aryl groups.

2. A polymerizable composition containing the sulfonium or oxosulfonium complex recited in claim 1 and a radical-polymerizable, ethylenically unsaturated compound.

3. A composition according to claim 2, wherein the sulfonium or oxosulfonium complex is contained in an amount of 0.01 to 30 parts by weight per 100 parts by weight of the radical-polymerizable, ethylenically unsaturated compound.

4. A composition according to claim 2, wherein a sensitizer which is to absorb any light in a region of from ultraviolet light to near infrared light is further contained.

5. A sulfonium complex according to claim 1 of the formula

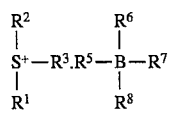

wherein $R^1, R^2, R^3, R^5, R^6, R^7$ and $R^8$ are as defined in claim 1.

6. A sulfonium complex according to claim 5 wherein $R^1$ is phenacyl and $R^2$ and $R^3$ are each methyl.

7. A polymerizable composition containing the sulfonium complex according to claim 5 and a radical-polymerizable, ethylenically unsaturated compound.

8. A polymerizable composition according to claim 7 wherein $R^1$ is phenacyl and $R^2$ and $R^3$ are each methyl.

* * * * *